United States Patent
Chen et al.

(10) Patent No.: US 9,750,614 B2
(45) Date of Patent: Sep. 5, 2017

(54) MEDICAL IMPLANT FOR FIXATION AND INTEGRATION WITH HARD TISSUE

(71) Applicant: LIFENET HEALTH, Virginia Beach, VA (US)

(72) Inventors: Jingsong Chen, Virginia Beach, VA (US); Dennis Phelps, Virginia Beach, VA (US); Andy T. Pritchard, Virginia Beach, VA (US); Nathan Kemper, Virginia Beach, VA (US); Thomas Brewer, Virginia Beach, VA (US)

(73) Assignee: Lifenet Health, Virginia Beach, VA (US)

( * ) Notice: Subject to any disclaimer, the term of this patent is extended or adjusted under 35 U.S.C. 154(b) by 0 days.

(21) Appl. No.: 14/776,255

(22) PCT Filed: Mar. 17, 2014

(86) PCT No.: PCT/US2014/030317
§ 371 (c)(1),
(2) Date: Sep. 14, 2015

(87) PCT Pub. No.: WO2014/145527
PCT Pub. Date: Sep. 18, 2014

(65) Prior Publication Data
US 2016/0038299 A1    Feb. 11, 2016

Related U.S. Application Data

(60) Provisional application No. 61/794,341, filed on Mar. 15, 2013.

(51) Int. Cl.
*A61F 2/44*    (2006.01)
*A61F 2/30*    (2006.01)

(52) U.S. Cl.
CPC .............. *A61F 2/442* (2013.01); *A61F 2/44* (2013.01); *A61F 2/4455* (2013.01);
(Continued)

(58) Field of Classification Search
CPC .. A61F 2002/30579; A61F 2002/30841; A61F 2002/4627
(Continued)

(56) References Cited

U.S. PATENT DOCUMENTS 5,562,669 A    10/1996    McGuire
6,458,158 B1   10/2002    Anderson et al.
(Continued)

FOREIGN PATENT DOCUMENTS

EP    1634552       3/2006
WO    2007079021    7/2007
(Continued)

OTHER PUBLICATIONS

Written Opinion and International Search Report issued in a corresponding International Application No. PCT/US2014/030317 dated Nov. 4, 2014.
(Continued)

*Primary Examiner* — Eduardo C Robert
*Assistant Examiner* — Tara R Carter
(74) *Attorney, Agent, or Firm* — RatnerPrestia

(57) ABSTRACT

The invention relates to medical implants, including spinal implants and bone grafts, for fixation and integration with hard tissue. The bone medical implants include at least one rotational fixation mechanism that further includes or is attached to one or more sharp protrusions configured to penetrate and become lodged into hard tissue to provide support and positional stability. Such support is useful to
(Continued)

ensure that the spinal bone graft may be used without additional stabilizing or anchoring structures, such as supporting plates or screws.

6 Claims, 38 Drawing Sheets

(52) U.S. Cl.
CPC ............ *A61F 2002/30004* (2013.01); *A61F 2002/3093* (2013.01); *A61F 2002/30354* (2013.01); *A61F 2002/30364* (2013.01); *A61F 2002/30405* (2013.01); *A61F 2002/30462* (2013.01); *A61F 2002/30579* (2013.01); *A61F 2002/30836* (2013.01); *A61F 2002/30841* (2013.01); *A61F 2002/30843* (2013.01); *A61F 2002/30846* (2013.01); *A61F 2002/30904* (2013.01); *A61F 2220/0016* (2013.01); *A61F 2310/00017* (2013.01); *A61F 2310/00023* (2013.01); *A61F 2310/00047* (2013.01); *A61F 2310/00179* (2013.01); *A61F 2310/00359* (2013.01)

(58) Field of Classification Search
USPC .................. 606/246–249; 623/17.11–17.16
See application file for complete search history.

(56) References Cited

U.S. PATENT DOCUMENTS

| | | | |
|---|---|---|---|
| 6,689,125 B1 | 2/2004 | Keith et al. | |
| 7,491,237 B2 | 2/2009 | Randall | |
| 7,744,597 B2 | 6/2010 | Gaskins et al. | |
| 8,292,958 B1 | 10/2012 | Bruffey et al. | |
| 8,317,866 B2 | 11/2012 | Palmatier et al. | |
| 2003/0078668 A1* | 4/2003 | Michelson | A61B 17/7059 623/17.16 |
| 2005/0049590 A1* | 3/2005 | Alleyne | A61F 2/442 623/17.11 |
| 2005/0107880 A1 | 5/2005 | Shrimp et al. | |
| 2006/0095136 A1* | 5/2006 | McLuen | A61F 2/4455 623/23.47 |
| 2006/0149385 A1 | 7/2006 | McKay | |
| 2008/0046090 A1 | 2/2008 | Paul et al. | |
| 2008/0065070 A1 | 3/2008 | Freid et al. | |
| 2008/0234827 A1 | 9/2008 | Schaller et al. | |
| 2009/0270873 A1 | 10/2009 | Fabian | |
| 2010/0137989 A1 | 6/2010 | Armstrong et al. | |
| 2010/0305706 A1 | 12/2010 | Webb et al. | |
| 2011/0035007 A1 | 2/2011 | Patel | |
| 2011/0160864 A1 | 6/2011 | Messerli et al. | |
| 2011/0196494 A1 | 8/2011 | Yedlicka et al. | |
| 2011/0202137 A1 | 8/2011 | Keith et al. | |
| 2011/0301712 A1 | 12/2011 | Palmatier et al. | |
| 2013/0166029 A1 | 6/2013 | Dinville et al. | |
| 2014/0121773 A1 | 5/2014 | Patel | |

FOREIGN PATENT DOCUMENTS

| | | |
|---|---|---|
| WO | 200727771 | 11/2007 |
| WO | 2011150350 | 12/2011 |

OTHER PUBLICATIONS

Exended European Search Report for European Application No. 14765130.1, dated Jan. 12, 2017, 12 pages.
Martz et al., "Materials and Design of Spinal Implants—A Review" Materials and Design of Spinal Implant Review, 1997, pp. 267-288.
Spinal Fusion, http://www.allaboutbackandneckpain.com/researchingtreatmentrecovery/print.asp?articleid=, dated Mar. 10, 2014—8 Pages.
http://www.medicalexpo.com/prod/ldr-medical/thoraco-lumber-screw-rod-units-posterier-8, dated Dec. 17, 2013—3 Pages.
da Vinci Surgical System, "http"//en.wikipedia.org/wiki/Da_Vinci_Surgical_System, Dated Dec. 31, 2013—5 Pages.

\* cited by examiner

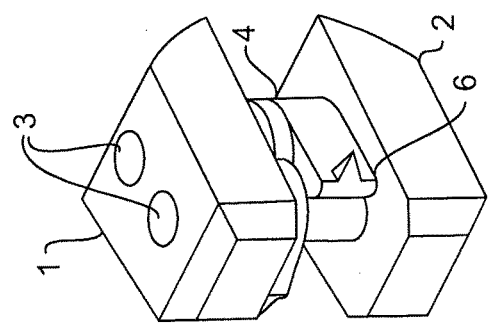
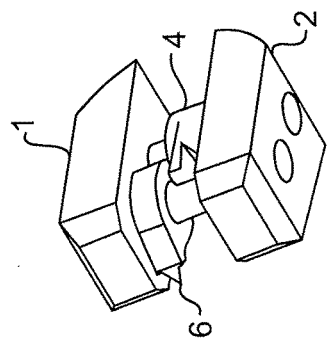
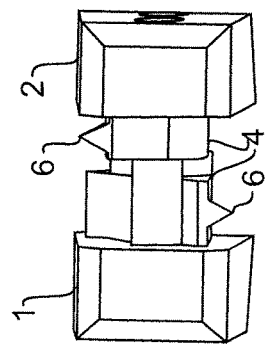
FIG. 5A
FIG. 5B
FIG. 5C

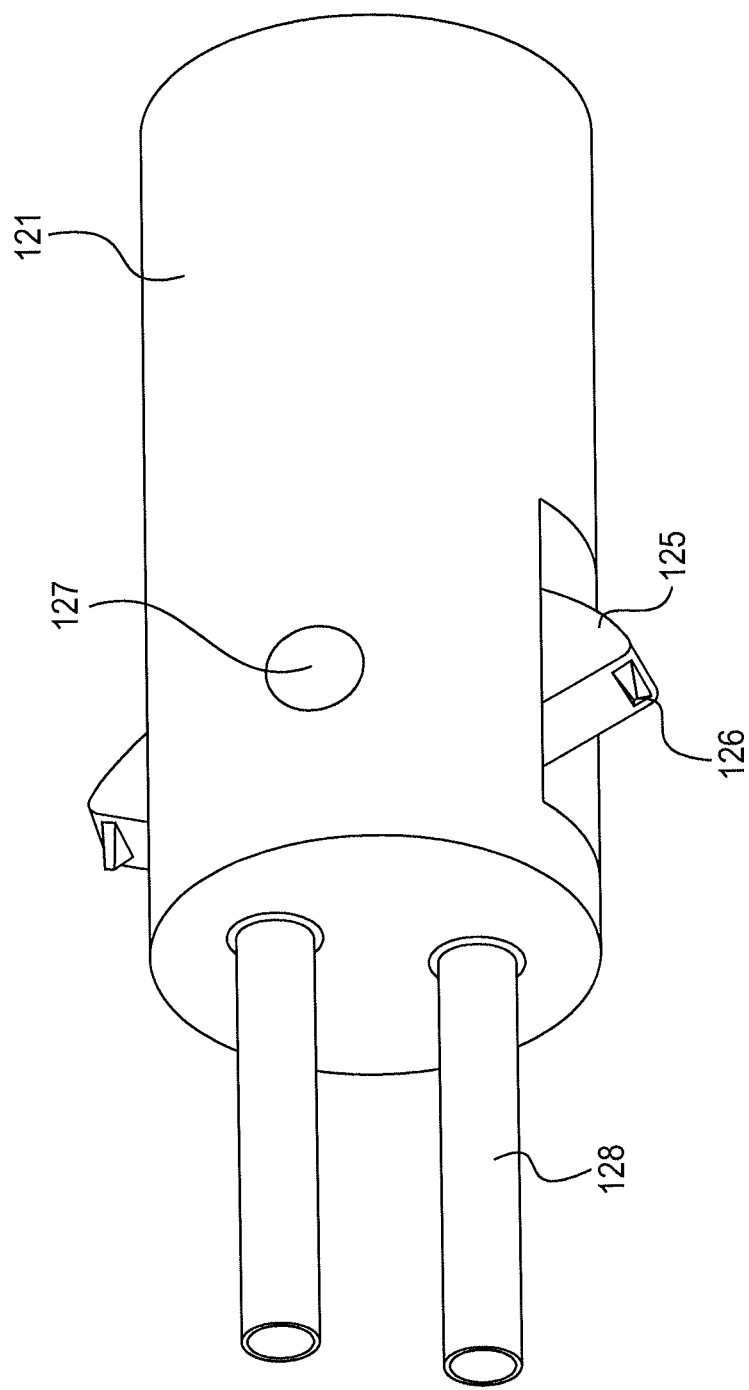

MEDICAL IMPLANT FOR FIXATION AND INTEGRATION WITH HARD TISSUE

FIELD OF THE INVENTION

This invention relates generally to medical implants useful for fixation and integration with hard tissue (e.g., bone tissue and cartilage tissue). More particularly, the invention relates to medical implants, including spinal implants and bone grafts, which are used in hard tissue fusion without the use of separate fixation or anchoring structures, such as supporting plates or screws. The medical implants of the invention, which may be composite or monolithic, include one or more fixation mechanisms as an integral component. The fixation mechanisms include one or more sharp protrusions configured to penetrate and become lodged into hard tissue at an integration site to provide further support and stabilization. For example, a sharp protrusion may penetrate and become lodged into a vertebral body to provide support and stabilization between fused vertebrae.

BACKGROUND OF THE INVENTION

The typical vertebra has a thick anterior bone mass called the vertebral body, with a neural (vertebral) arch that arises from the posterior surface of the vertebral body. The central portions of adjacent vertebrae are supported by intervertebral discs. The spinal disc and/or vertebral bodies may be displaced or damaged due to trauma, disease, degenerative defects, or wear over an extended period of time. One result of this displacement or damage to a spinal disc or vertebral body may be chronic back pain. In many cases, to alleviate back pain from degenerated of herniated discs, the disc is removed along with all or part of at least one neighboring vertebrae and is replaced by an implant that promotes fusion of the remaining bony anatomy. However, the success or failure of spinal fusion may depend upon several factors. For instance, the spacer or implant used to fill the space left by the removed disc and bony anatomy must be sufficiently strong to support the spine under a wide range of loading conditions. The spacer should also be configured so that it likely to remain in place once it has been positioned in the spine by the surgeon. Additionally, the material used for the spacer should be biocompatible and should promote bone growth and integration.

An additional support system, such as a system including plates and/or screws, is typically used in combination with spacers to further stabilize the spine during the fusion process. These devices, commonly referred to as bone fixation plating systems, typically include one or more plates and screws for aligning and holding vertebrae in a fixed position with respect to one another. Plating systems that are independent of the spacers often present additional failure modes for the spinal fusion process. For example, the screws may loosen over time, or the hardware may fail due to other means, such as breakage.

Similar problems arise with medical implants which integrate with hard tissue at other locations in the body. Such medical implants may be used, for example, in a knee, shoulder, elbow, wrist, ankle, hip, or finger.

Given the problems discussed above, there is a need for a spine stabilization system that promotes fusion of adjacent vertebrae while at the same time providing stabilization of the spinal area where fusion occurs. Thus, there is a need for a spinal implant or bone graft that addresses the problems associated with using separate spacers and stabilization systems.

More broadly, there is a need for medical implants used without separate stabilization systems that are useful for fixation and integration with hard tissue at other locations in the body. Accordingly, one aspect of the invention is to provide such an implant and a method for using the same. Other embodiments will be apparent from the following description of the invention.

SUMMARY OF THE INVENTION

According to one aspect of the invention, a medical implant for fixation and integration with hard tissue (e.g., bone tissue and cartilage tissue) is provided at an integration site. The integration site may include, for example, a vertebra (including a vertebral body), a knee, a shoulder, an ankle, an elbow, a wrist, a hip or a finger. Certain embodiments of the invention relate to integration at the vertebrae. Such a process may be further described as spine fixation, anterior column fusion, spinous process fusion, and facets fusion.

According to one aspect of the invention, a medical implant is provided for implantation into a host. More specifically, a compound medical implant is provided for fixation and integration with hard tissue, the implant comprising one or more rotational fixation mechanisms substantially centered on an axis (e.g., a pin or a rod); and one or more sharp protrusions attached to each of the one or more rotational fixation mechanisms, each sharp protrusion designed to penetrate and become lodged into hard tissue at an integration site.

In another embodiment, a spinal implant is provided for fixation and integration with a vertebral body, the spinal implant including a first portion having an inferior and superior surface; a second portion having an inferior and superior surface; one or more biocompatible pins for holding together the first portion and the second portion; and one or more rotational fixation mechanisms located between the first portion and the second portion, the rotational fixation mechanisms including an opening through which the one or more pins traverse. The one or more rotational fixation mechanisms comprise at least one sharp protrusion configured to penetrate and become lodged into a vertebral body. In one embodiment, the sharp protrusion is configured to penetrate and become lodged into the end plate of a vertebra. In another embodiment, the end plate is removed prior to implantation and the sharp protrusion is configured to penetrate and become lodged into adjacent bone or hard tissue.

In one embodiment, the sharp protrusion may have a pyramidal shaped cross-section. In another embodiment, the sharp protrusion may have cross-sections having other geometrical configurations, including, but not limited to, circular, oval or knife-like cross-sections.

In one embodiment, all of the components (e.g., the first and second portion, the pins and the rotational fixation mechanisms) are independently made of cortical bone, a biocompatible metal and a biocompatible polymer (e.g., polyether ether ketone (PEEK)). In one embodiment, all of the components may be made of cortical bone.

In one embodiment, the first and second portion and the pins may be made of cortical bone, and the rotational fixation mechanisms may be made of a biocompatible metal or PEEK. In one embodiment, the rotational fixation mechanisms are made of a biocompatible metal.

In one embodiment, the sharp protrusion may have a length ranging from about 0.1 mm to about 4 cm. The length is measured from the center of the axis (e.g., pin or rod) to the tip of the sharp protrusion. In one embodiment, the sharp protrusion may have a length ranging from about 0.1 mm to about 1.5 cm. In another embodiment, the sharp protrusion may have a length ranging from about 0.5 mm to about 0.8 cm.

The sharp protrusion may penetrate a vertebral body at an angle ranging from about 15° to about 90° with respect to a planar face of the vertebral body. In another embodiment, the sharp protrusion may penetrate a vertebral body at an angle ranging from about 30° to about 60°. In another embodiment, the sharp protrusion may penetrate a vertebral body at an angle from about 40° to 50°.

According to another aspect of the invention, a textured spinal implant is provided for implantation into a host. The textured implant includes a base member including a void space or through section (e.g., a key-shaped void space) and one or more textured surfaces configured to contact a portion of the host bone; a biocompatible pin approximately parallel to the surfaces and perpendicular to the void space or through section (e.g., key-shaped void space) at its narrow portion; and a rotational fixation mechanism having an opening through which the pin traverses. The rotational fixation mechanism includes at least one sharp protrusion which exceeds the height of the textured surface and is configured to penetrate a vertebral body. The sharp protrusion may exceed the height of the textured surface.

In one embodiment, the base member is comprised of cortical bone.

In one embodiment, the rotational fixation mechanism is comprised of a biocompatible metal.

In one embodiment, the remaining portion of the void space is filled with cancellous bone or other osteoconductive substances or matrices. Matrices may be derived from natural sources or they may be synthetic or a mixture of both. Matrices from natural sources may also comprise natural polymers, including, but not limited to, collagen, hyaluronic acid, alginate, albumin, fibrinogen-fibrin, chitosan, elasin, laminin, connective tissues, cortical or cancellous bone, demineralized or mineralized bone, fascia lata, dermis, muscle, ligament, tendon, a mixture thereof, and a mixture of reconstituted tissue. Matrices from synthetic sources refer to any material not produced by living organisms, which may include, but are not be limited to, the synthetic material made up of organic components, inorganic components, or a mixture thereof. In some embodiments, a synthetic matrix may comprise an organic synthetic polymer, such as poly(lactic-co-glycolic acid), polycaprolactone (PCL), polyglycolic acid (PGA), polylactic acid (PLA), polyhydroxybutyrate (PHB), Polyethylene glycol) (PEG), poly(ethylene oxide) (PEO)), and others. In some embodiments, a tissue, an organ, or matrix comprising at least one of alginate, chitosan, collagen, gelatin, hyaluronic acid, a fibronectin, an elastin, a laminin, and a proteoglycan may be employed. In certain embodiments, a matrix comprising inorganic components, such as hydroxyapatite, calcium sulfate, octacalcium phosphate, calcium phosphate, macroporous calcium metaphosphate ceramic, β-tricalcium phosphate, metal, metal alloy, and others, may be used. A matrix used in certain embodiments of the present invention may be prepared by demineralizing, decellularizing or devitalizing a tissue or an organ, and cells may be seeded onto the matrix.

According to another aspect of the invention, a bone graft is provided for implantation into a host. The bone graft includes a monolithic cortical bone ring-like body having a substantially central void space and configured to contact a portion of the host bone; one or more biocompatible pins traversing the opening in the cortical bone ring-like body; and one or more rotational fixation mechanisms located within the void space in the cortical bone ring-like body, the one or more rotational fixation mechanisms including an opening through which the one or more pins traverse. The one or more rotational fixation mechanisms include at least one sharp protrusion configured to penetrate a vertebral body.

According to another aspect of the invention, a spinal bone graft is provided for implantation into a host. The bone graft includes a composite cortical bone ring-like body having a substantially central void space and including two or more distinct, adjacent cortical bone portions, each portion including a face complimentary to a face on an adjacent cortical bone portion. Each face includes a single projection or a single depression such that the adjacent faces are complimentary and a single projection interlocks with a single depression to provide an interlocking fit between said adjacent bone portions. The bone graft further includes one or more biocompatible pins traversing the void space in the cortical bone ring-like body and one or more rotational fixation mechanisms located within the void space in the cortical bone ring-like body, the one or more rotational fixation mechanisms comprising an opening through which the one or more pins traverse. The one or more rotational fixation mechanisms include a sharp protrusion configured to penetrate a vertebral body.

BRIEF DESCRIPTION OF THE DRAWINGS

FIGS. 5A, 5B and 5C present different views of an assembled stand-alone composite spinal implant according to one embodiment of the present invention.

FIG. 34 presents a perspective view of a composite medical implant according to one embodiment of the invention.

DETAILED DESCRIPTION OF THE INVENTION

Figure 1:
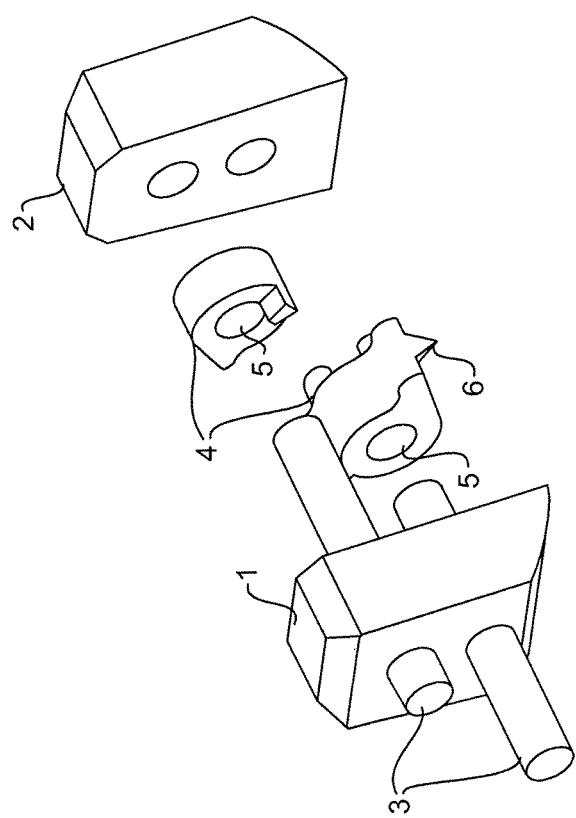
FIG. 1 presents a perspective view of a disassembled composite spinal implant according to one embodiment of the present invention.
Figure 2:
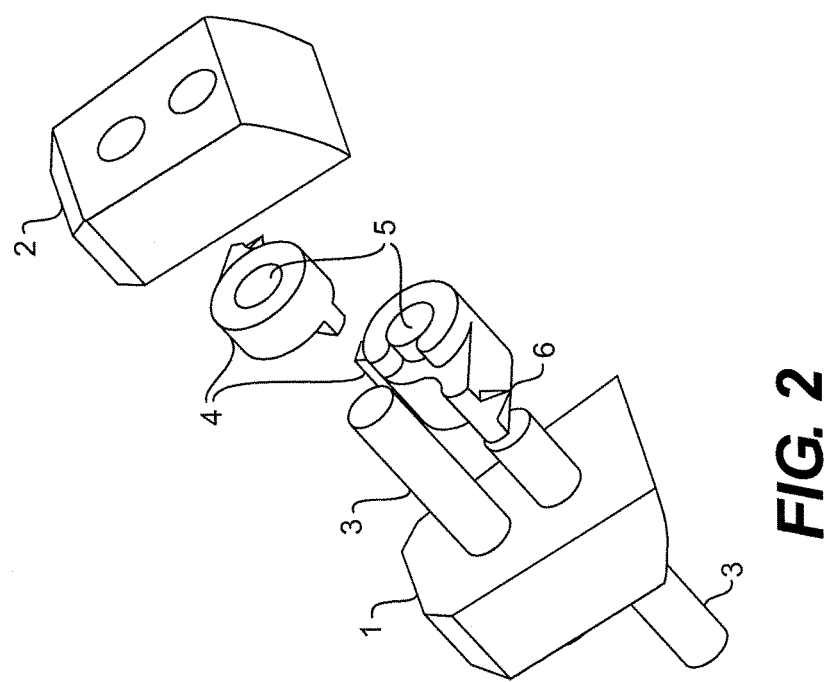
FIG. 2 presents another perspective view of a disassembled composite spinal implant according to one embodiment of the present invention.
Figure 3:
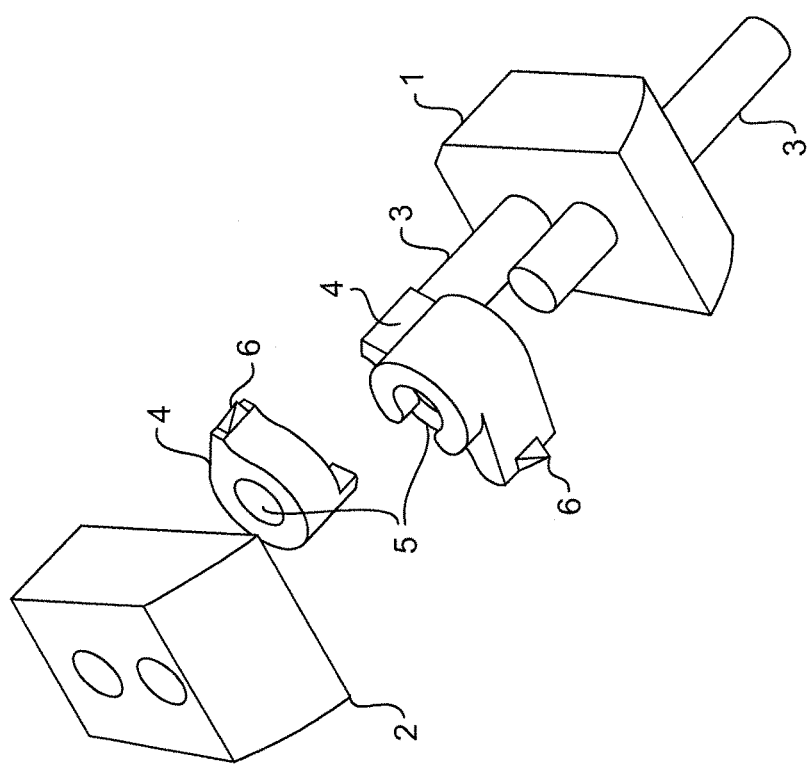
FIG. 3 presents another perspective view of a disassembled composite spinal implant according to one embodiment of the present invention.
Figure 4:
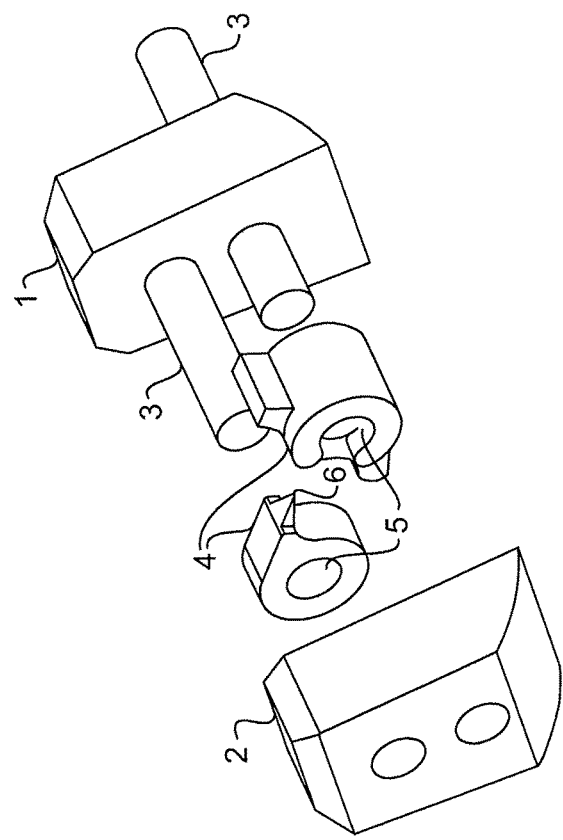
FIG. 4 presents another perspective view of a disassembled composite spinal implant according to one embodiment of the present invention.

The present invention provides medical implants, including spinal implants and spinal bone grafts, useful for fixation and integration with hard tissue (e.g., bone or cartilage tissue). Importantly, the medical implants may be used in the absence of separate fixation or anchoring structures, such as supporting plates or screws. For example, in one embodiment, the invention provides for spinal implants to fuse together adjacent vertebral bodies while maintaining the natural curve of the spine and the proper spacing between the adjacent vertebral bodies. The implant has a size and a geometry that enables it to be efficiently installed and to remain securely placed between adjacent vertebral bodies until healing and fusion take place. Moreover, the spinal implants and bone grafts may be used in spinal fusion without the further use of stabilization structures, e.g., supporting plates or screws.

Referring more specifically to the drawings, FIGS. 1-4 provide varying perspective views of a disassembled composite spinal implant according to the present invention. A first portion (1) and a second portion (2) are provided, each having an inferior and a superior surface. One or more biocompatible pins (3) may be used to hold together the first and second portion. One or more rotational fixation mechanisms (4) may be located between the first portion and the second portion. The rotational fixation mechanisms may comprise an opening (5) through which the one or more pins traverse to secure the rotational fixation mechanisms in place. The rotational fixation mechanisms include at least one sharp protrusion (6) configured to penetrate a vertebra. This is useful for providing stabilization of the spinal area where fusion occurs, and the resultant spinal bone graft may be used without additional stabilizing structures, such as supporting plates or screws.

The sharp protrusion (6) may have different cross-sectional profiles. For example, in one embodiment, the sharp protrusion has a pyramidal shaped cross-section. In another embodiment, the sharp protrusion has a circular, oval, or knife-like cross-section.

The various components of the composite implant, independently, may be made of different materials, natural and synthetic, including, but not limited to, cortical bone, biocompatible metals, ceramics and biocompatible polymer. Examples of suitable metals include but are not limited to titanium, aluminum, stainless steel, or alloys (e.g., Ti6Al-4V). Ceramics may include but are not limited to glass-ceramics and apatite-wollastonite ceramics. Polymers may include but are not limited to polysiloxane modified styrene-ethylene/butylene block copolymer or polyether ether ketone (PEEK).

The implants may further comprise bone graft substitutes, including but not limited to hydroxyapatite, tricalcium phosphate (TCP) and osteoinductive growth factors (bone morphogenetic protein, BMP, and transforming growth factor, TGFβ), and/or cells. The cells may be differentiated cells, progenitor cells, or stem cells. The stem cells may be adult stem cells or pluripotent stem cells. The progenitor cells or the adult stem cells may be derived from placenta, bone marrow, adipose tissue, blood vessel, amniotic fluid, synovial fluid, synovial membrane, pericardium, periosteum, endosteum, dura, peripheral blood, umbilical blood, menstrual blood, baby teeth, nucleus pulposus, brain, skin, hair follicle, intestinal crypt, neural tissue, or muscle. The growth factor can be truncated growth factors as described in US Published Application Nos. US2013/0090290, US2013/0196910A1 and US2013/0196909A1, and WO2013033680.

In one embodiment of the invention, all of the components (i.e., the first and second portion, the one or more pins and the one or more rotational fixation mechanisms) are made of cortical bone.

In another embodiment of the invention, the first portion, the second portion and the pins are made of cortical bone.

In one embodiment of the invention, the rotational fixation mechanism is made of a biocompatible metal.

FIGS. 5A, 5B and 5C provide views of the assembled composite spinal implant. The one or more rotational fixation mechanisms may include at least one sharp protrusion. In one embodiment, the sharp protrusion as a length ranging from 0.1 mm to about 4 cm. In one embodiment, the sharp protrusion may have a length ranging from about 0.1 mm to about 1.5 cm. In another embodiment, the sharp protrusion has a length ranging from about 0.5 mm to about 0.8 cm.

The rotational fixation mechanisms may rotate about the pin prior to final assembly. At final assembly or when the rotational fixation mechanisms are implanted into a host during surgery, the rotational fixation mechanisms are locked in place so that they may stabilize the spinal implant when it is positioned in the spine.

In an embodiment of the invention, the fully assembled spinal implant as discussed above has built in void space between the pins (3) and the rotational fixation mechanisms (4). This has a number of functions, including allowing space for to promote fusion between the two vertebral bodies or adjacent hard tissue.

In one embodiment of the invention, the at least one sharp protrusion penetrates a vertebrae at an angle ranging from about 15° to about 90° with respect to a planar face of the vertebral bodies. In another embodiment, the sharp protrusion may penetrate a vertebral body at an angle ranging from about 30° to about 60°. In another embodiment, the sharp protrusion may penetrate a vertebral body at an angle from about 40° to 50°.

Figure 6:
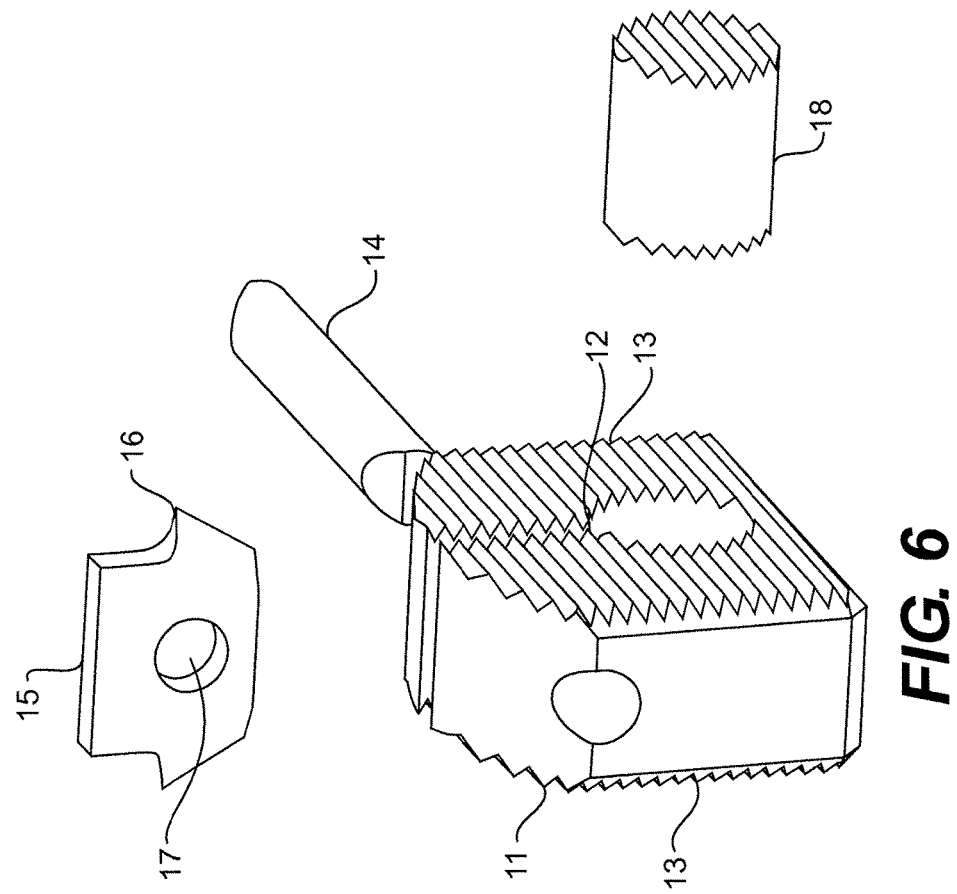
FIG. 6 presents a perspective view of a disassembled textured spinal implant according to one embodiment of the present invention.
Figure 7:
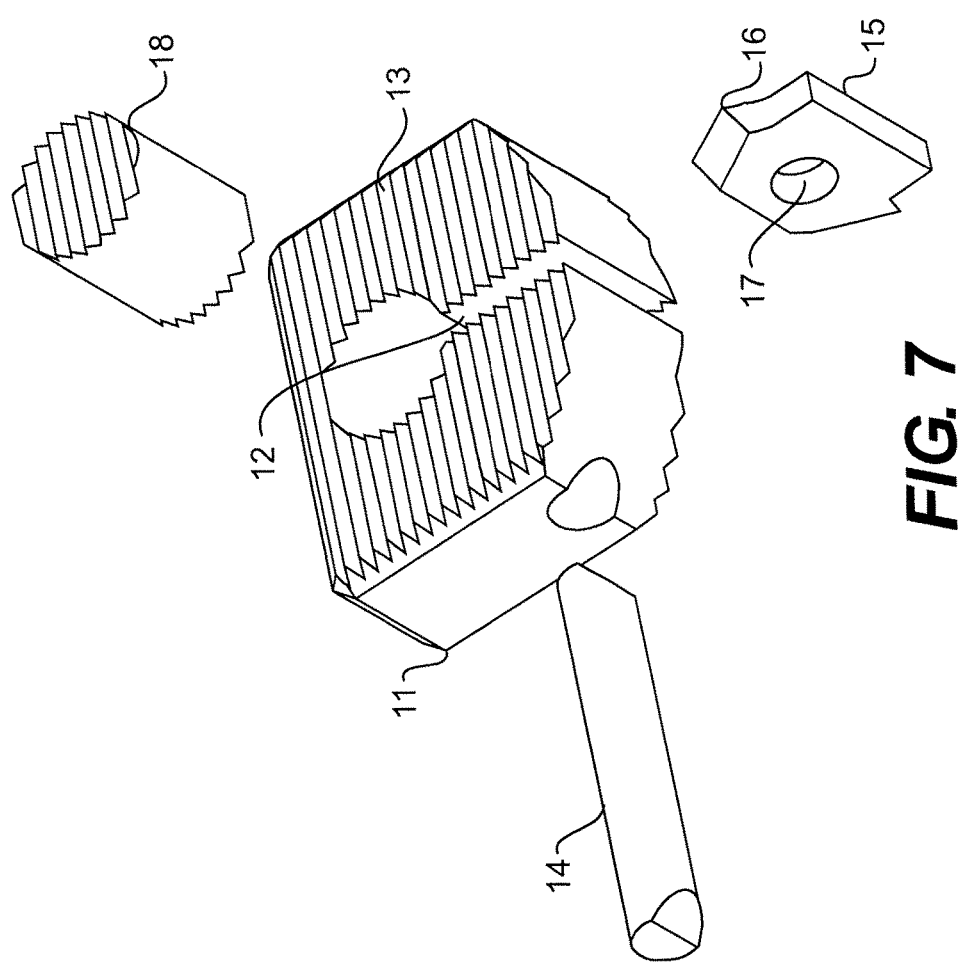
FIG. 7 presents another perspective view of a disassembled textured spinal implant according to one embodiment of the present invention.
Figure 8:
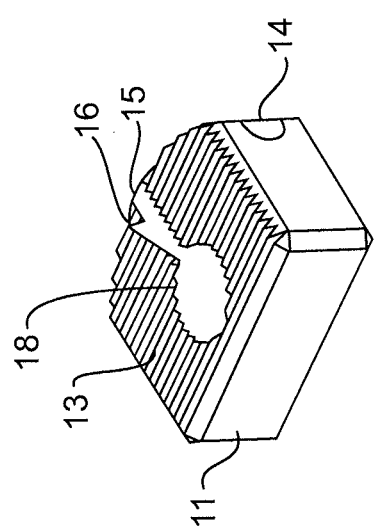
FIG. 8 presents a perspective view of an assembled textured spinal implant according to one embodiment of the present invention.

FIGS. 6a, 6b and 7 provide views of a disassembled textured spinal implant. FIG. 8 provides a view of an assembled textured spinal implant. The textured spinal implant includes base member (11), a biocompatible pin (14), and one or more rotational fixation mechanisms (15). Base member (11) includes a key-shaped through-section or void space (12) and one or more textured surfaces (13) configured to contact a portion of the host bone. A biocompatible pin (14) is approximately parallel to the surfaces and perpendicular to the key-shaped through-section at its narrow portion. The one or more rotational fixation mechanisms (15) have an opening (17) through which the pin traverses, the one or more rotational fixation mechanisms including at least one sharp protrusion (16) configured to penetrate a vertebral body to provide positional stability. The at least one sharp protrusion exceeds the height of the textured surface.

In one embodiment of the invention, the textured spinal implant comprises two rotational fixation mechanisms, one having a sharp protrusion configured to penetrate and become lodged into the vertebral body above the implant and the other having a sharp protrusion configured to penetrate and become lodged into the vertebral body below the implant, thus providing fixation and positional stability of the implant between the two vertebral bodies. In one embodiment, the two rotational fixation mechanisms may be connected to one another. In another embodiment, the two rotational fixation mechanisms may be configured to act independently of one another to provide positional stability of the implant between two vertebrae.

The remaining portion of the void space (i.e., the portion of the void space remaining after the rotational fixation mechanism is located in place) may be filled (18) with cancellous bone or other osteoconductive materials (e.g., hydroxyapatite, tricalcium phosphate (TCP) with or without osteoinnductive growth factors (bone morphogenetic protein, BMP, and transforming growth factor, TGFβ), and/or cells).

In one embodiment, the sharp protrusion has a length ranging from 0.1 mm to about 4 cm. In one embodiment, the sharp protrusion may have a length ranging from about 0.1 mm to about 1.5 cm. In another embodiment, the sharp protrusion has a length ranging from about 0.5 mm to about 0.8 cm.

Figure 9:
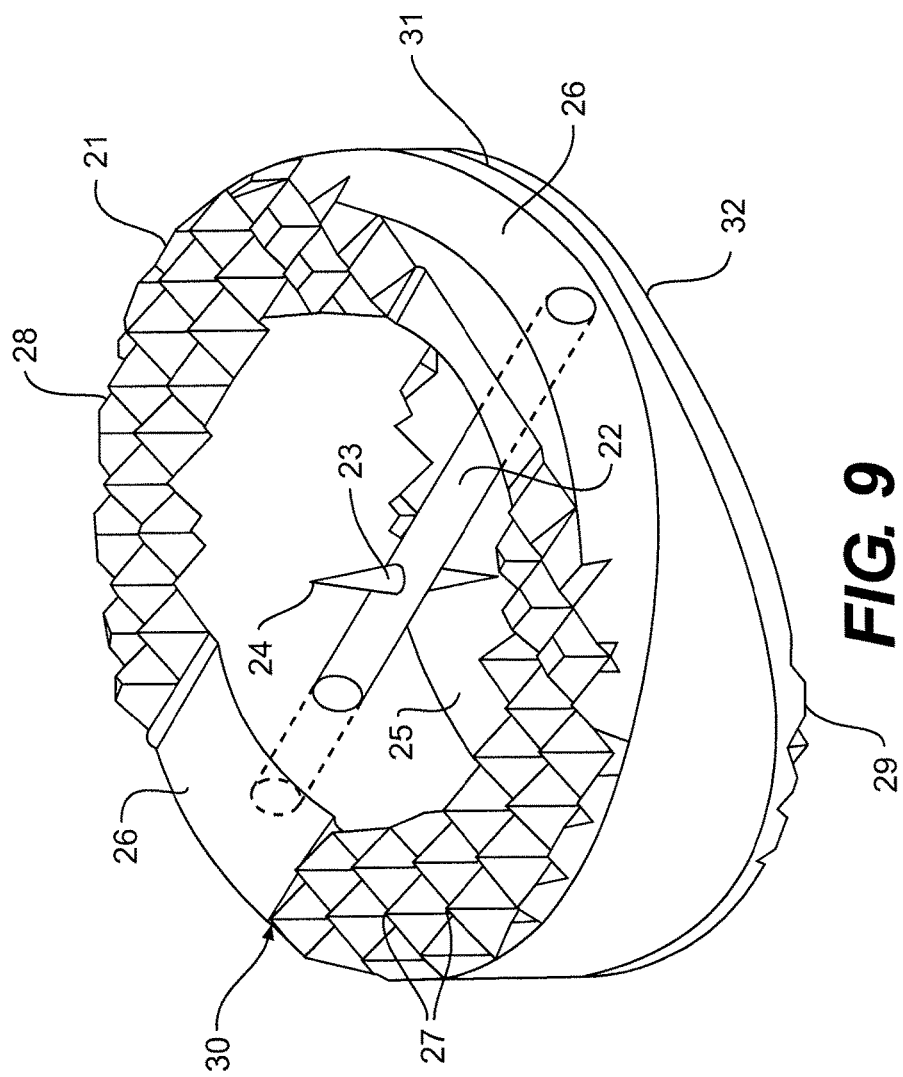
FIG. 9 presents a perspective view of an assembled spinal bone graft according to one embodiment of the present invention.

FIG. 9 provides a view of an assembled spinal implant for implantation into a host. The graft of this embodiment is a solid annular ring-like body (21) having a substantially central through hole or void space (25). The body has opposed superior (28) and inferior (29) surfaces and anterior and posterior ends (30), (31). At least a portion of the superior and inferior surfaces includes a plurality of bone engaging protrusions (27). These protrusions may be discrete. The superior and inferior surfaces each may include one or more zones or regions (26) that are free of any bone-engaging protrusions. The posterior end of the implant may include a tip (32) that is formed of converging portions of the superior and inferior surfaces.

One or more biocompatible pins (22) may traverse the central opening in the ring-like body. One or more rotational fixation mechanisms (23) are located within the central opening on the one or more pins, the one or more rotational fixation mechanisms including at least one sharp protrusion (24) configured to penetrate a vertebral body. The sharp protrusion may have different cross-sectional profiles. In one embodiment, the pin is fully rotatable.

In one embodiment, the sharp protrusion has a pyramidal shaped cross-section. In one embodiment, the sharp protrusion has a pyramidal shaped cross-section. In another embodiment, the sharp protrusion has a circular, oval, or knife-like cross-section.

The body of the spinal graft of this embodiment may be made of cortical bone and thus may be referred to as a bone graft.

In another embodiment, the body of the spinal graft of this embodiment may be made of a biocompatible metal (e.g., titanium or Ti6Al-4V), a ceramic (e.g., glass-ceramics and apatite-wollastonite ceramics) or a biocompatible polymer (e.g., PEEK or polysiloxane modified styrene-ethylene/butylene block copolymer).

The various other components of this embodiment, independently, may be made of different materials, including, but not limited to, cortical bone, a biocompatible metal and a biocompatible polymer (such as polyether ether ketone (PEEK)).

In one embodiment of the invention, the rotational fixation mechanism is made of a biocompatible metal.

Figure 10:
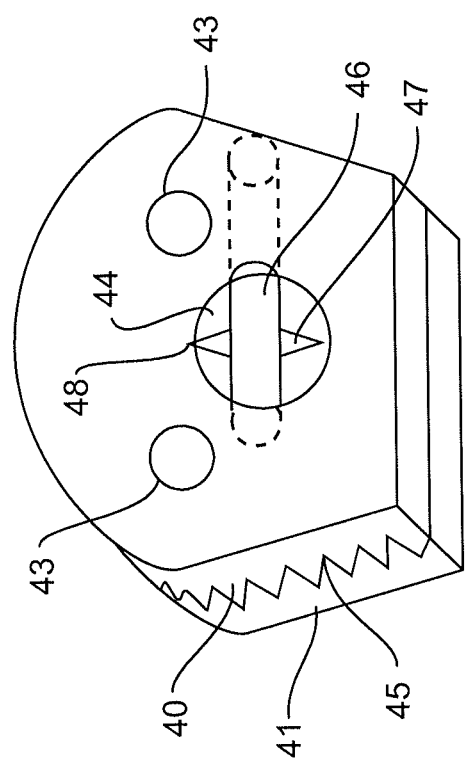
FIG. 10 presents a perspective view of an assembled spinal bone graft according to one embodiment of the present invention.

FIG. 10 illustrates a perspective view of a wedge composite bone graft (flattened curved wedge composite bone graft). The flattened curved wedge composite bone graft includes first and second cortical bone portions (40), (41) held together by two cortical bone pins (43) to form a pinned graft unit, and the pinned graft unit having an void space (44) disposed therethrough located between pins (43). The cortical bone portions (40), (41) are patterned with grooves (45) running in direction to provide an interlocking fit between the bone portions.

One or more biocompatible pins (46) may traverse the central void space in the cortical bone ring-like body. One or more rotational fixation mechanisms (47) are located within the central void space on the one or more pins, the one or more rotational fixation mechanisms including at least one sharp protrusion (48) configured to penetrate a vertebral body.

Figure 11:
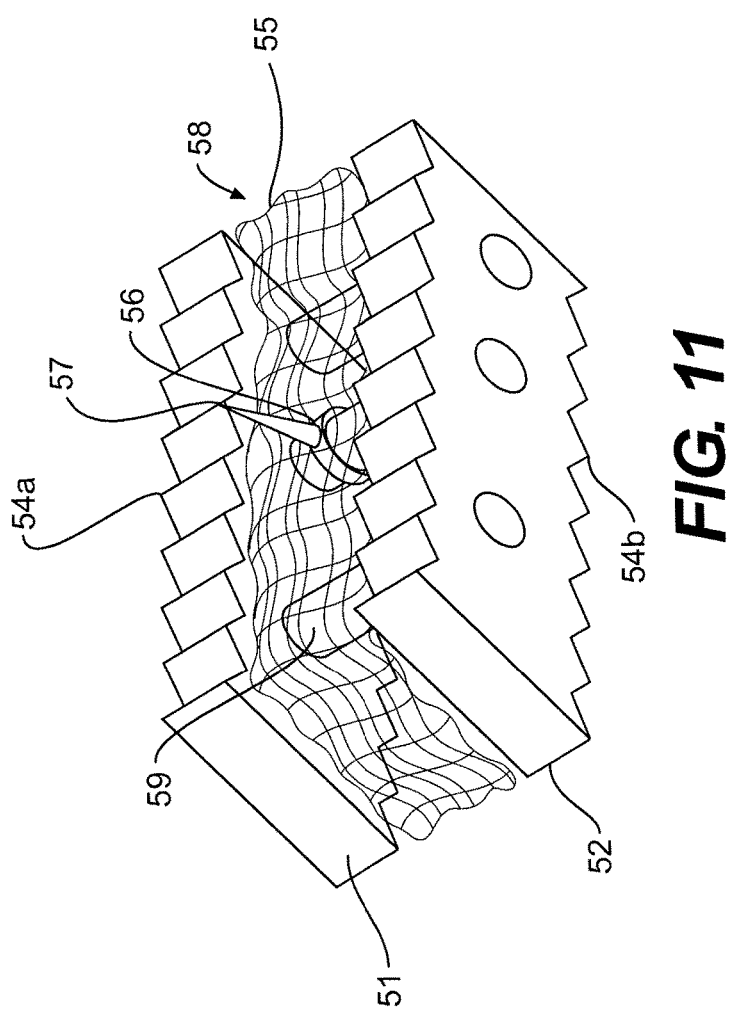
FIG. 11 presents a perspective view of an assembled spinal bone graft according to the present invention.
Figure 12:
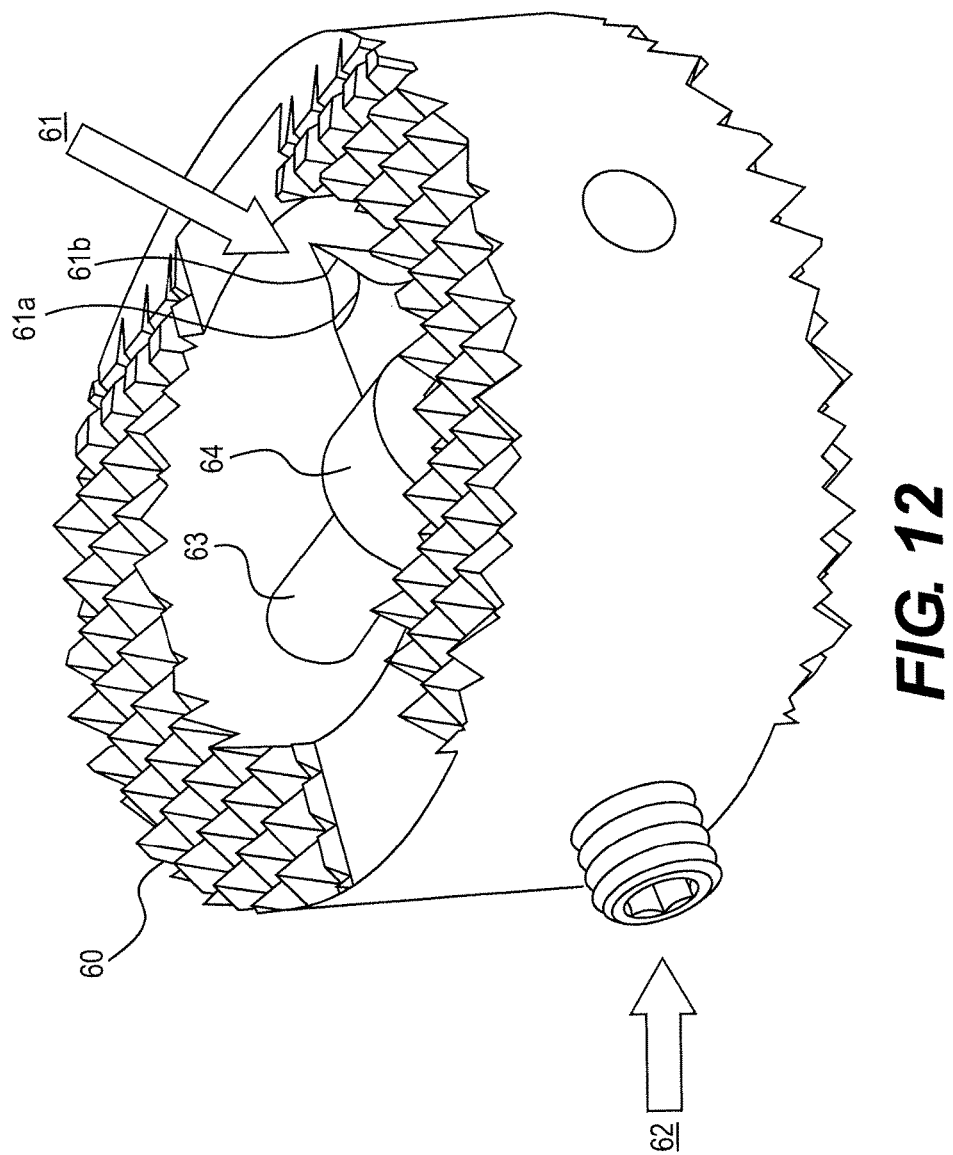
FIG. 12 presents a perspective view of a textured spinal implant according to one embodiment of the invention, including a double angled sharp protrusion and a screw used to urge a rotational fixation mechanism to implant the sharp protrusion into hard tissue.
Figure 13:
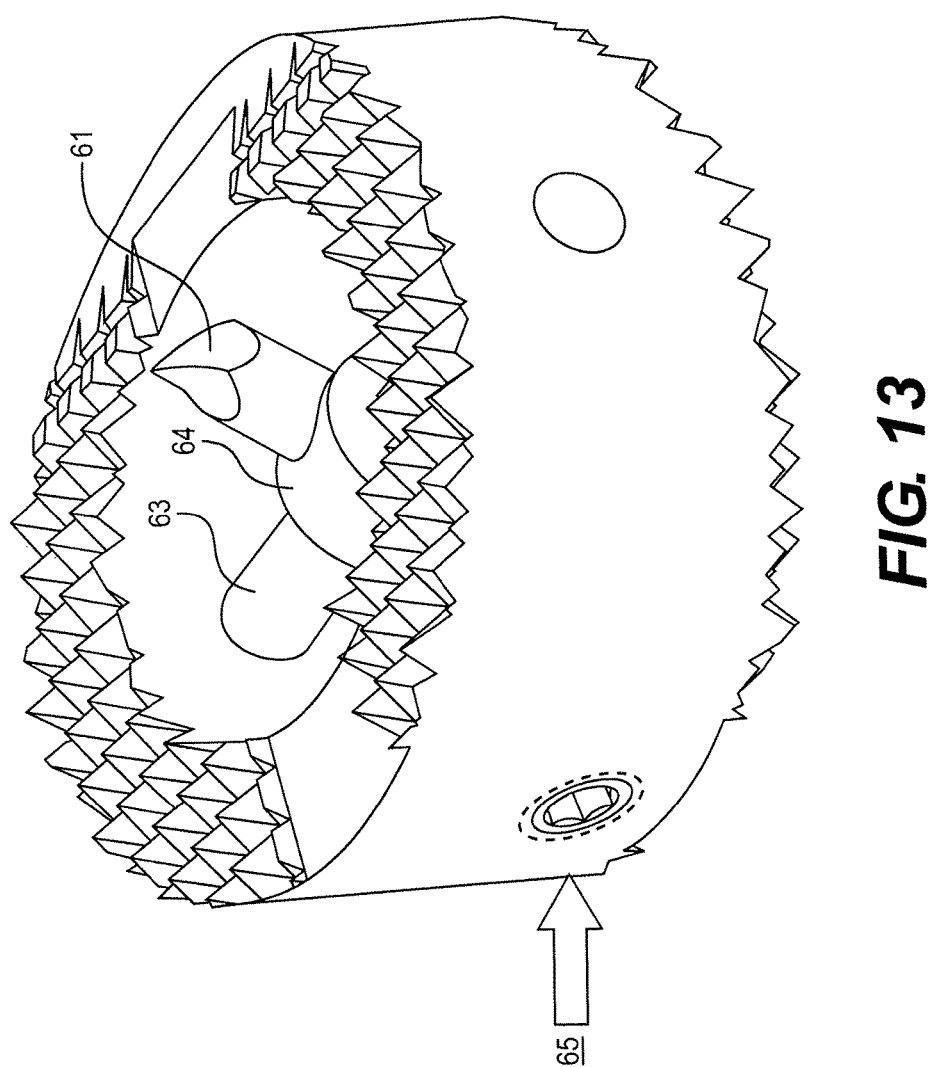
FIG. 13 presents a perspective view of a textured spinal implant according to one embodiment of the invention.
Figure 14:
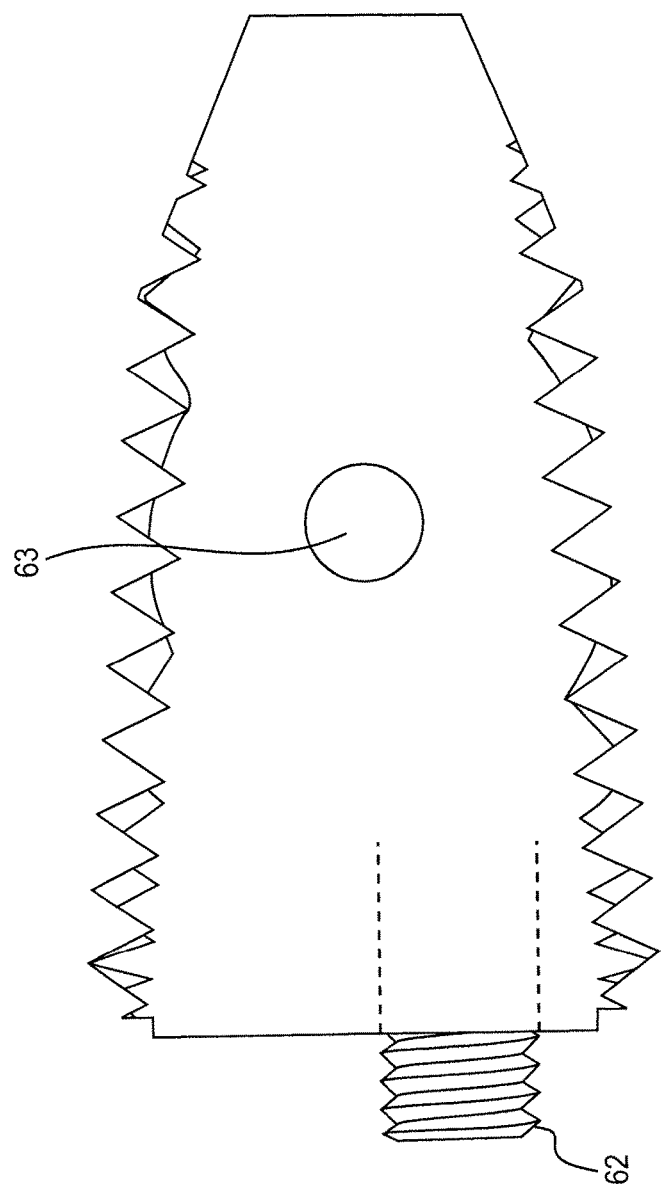
FIG. 14 presents a side view of a textured spinal implant according to one embodiment of the invention.

FIG. 11 shows a perspective view of a rectangular block composite bone graft, including a first cortical bone portion (51), a second cortical bone portion (52), a void space (58) disposed between cortical bone portions (51) and (52), through-holes (53), and biocompatible pins (e.g., cortical bone pins) (59). The void space (58) includes one or more therapeutically beneficial substances (55). The composite bone graft includes opposing textured surfaces (54*a*) and (54*b*) provided perpendicular to the interfaces of the bone portions (51) and (52), with the therapeutically beneficial substance (55), and defining a saw-tooth-like pattern. The therapeutically beneficial substances may include, but are not limited to, cancellous bone or other osteoconductive materials (e.g., hydroxyapatite, tricalcium phosphate (TCP) and osteoconductive growth factors (bone morphogenetic protein, BMP, and transforming growth factor, TGFβ)).

One or more biocompatible pins (59) may traverse the void (58) disposed between cortical bone portions (51) and (52). One or more rotational fixation mechanisms (56) are located within the void on the one or more pins, the one or more rotational fixation mechanisms including at least one sharp protrusion (57) configured to penetrate a vertebral body. The sharp protrusion may have different cross-sectional profiles.

In an embodiment of the invention, the spinal implants and bone grafts provided in FIGS. 1-5 and 9-11 have sharp protrusions that penetrate the vertebral body in a substantially perpendicular plane.

In one embodiment, the method of the claimed invention incorporates use of a da Vinci surgical system to implant the spinal implant into the patient during surgery.

Figure 15:
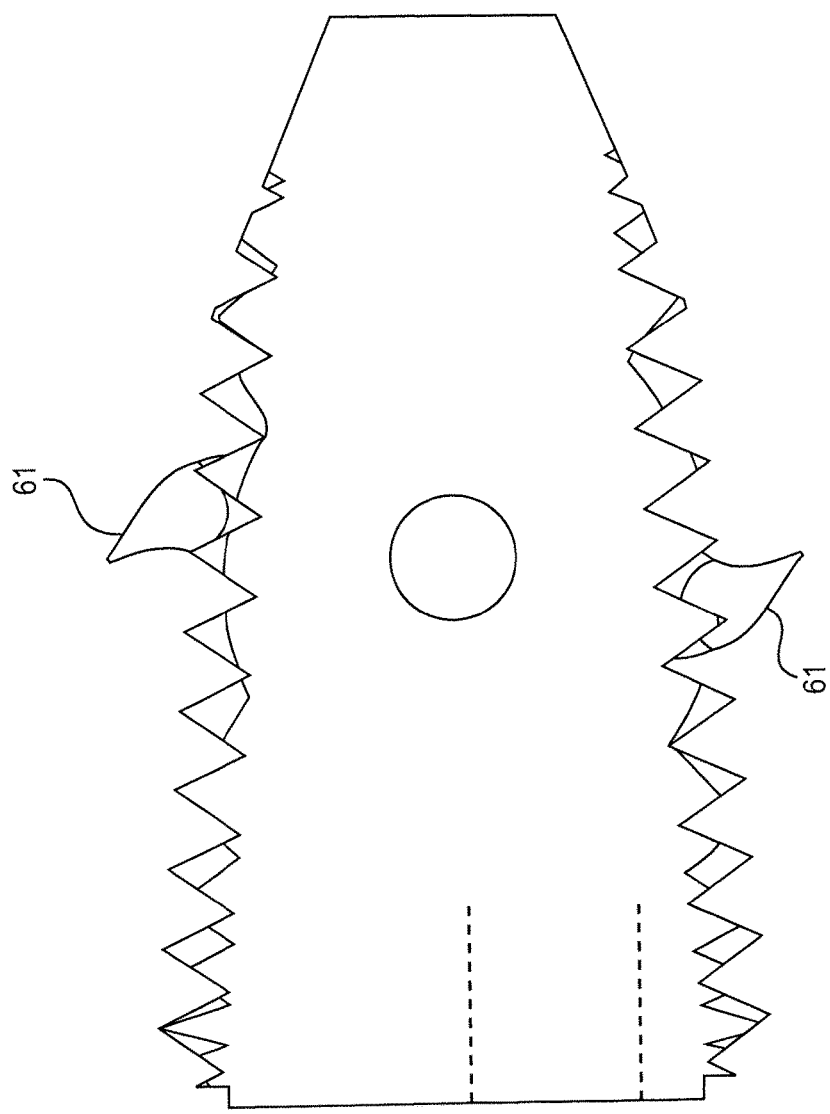
FIG. 15 presents a side view of a textured spinal implant according to one embodiment of the invention.
Figure 16:
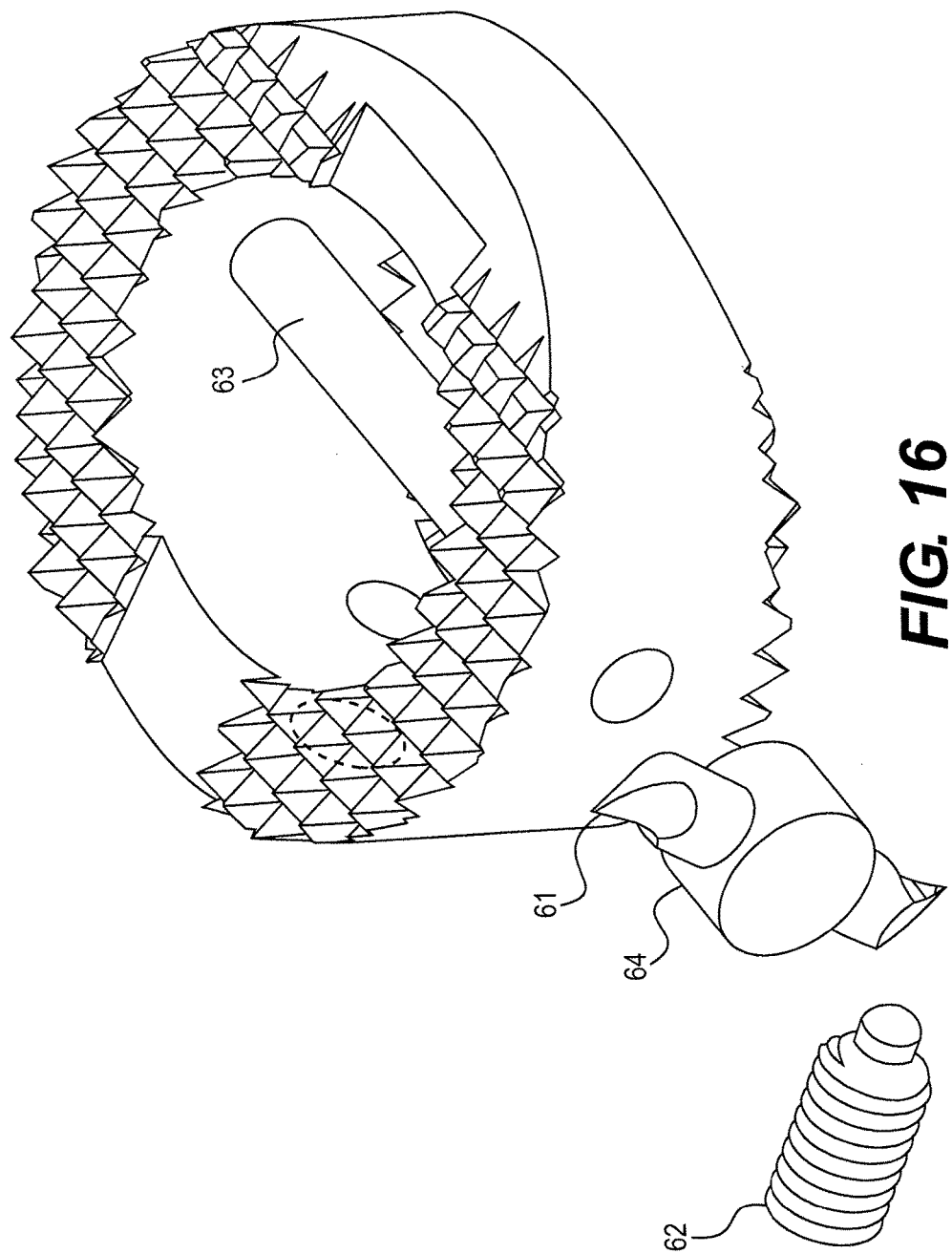
FIG. 16 presents a perspective view of a textured spinal implant according to one embodiment of the invention. Several of the parts are shown disassembled.
Figure 17:
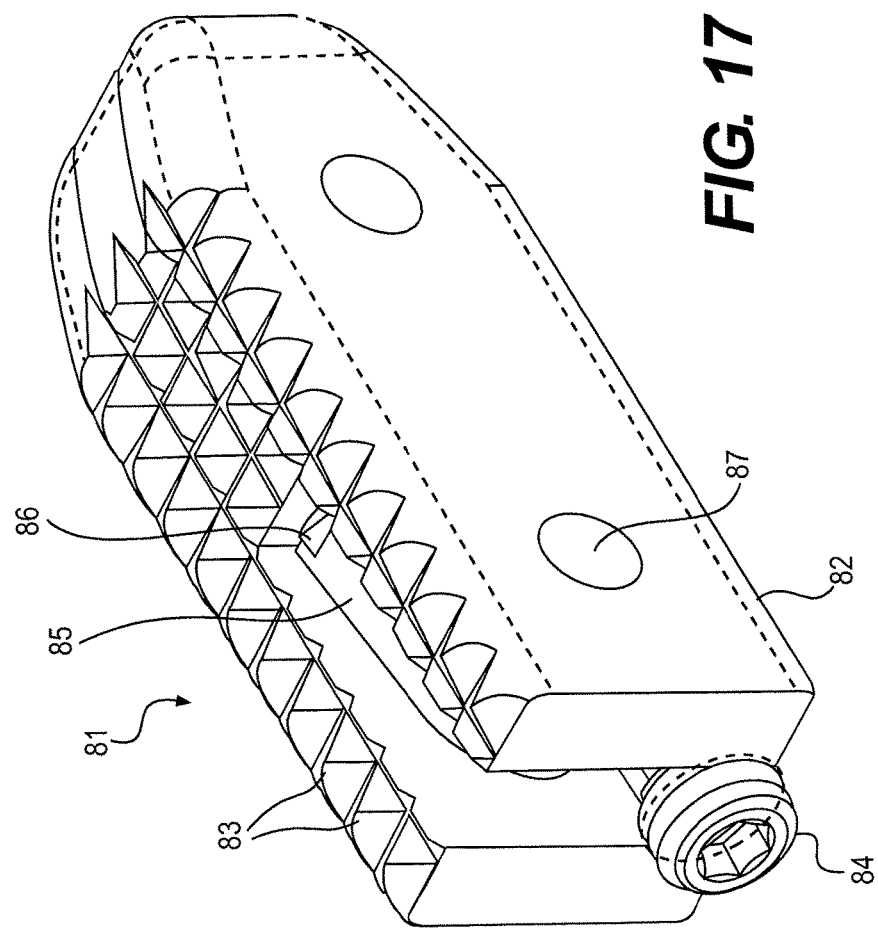
FIG. 17 presents a perspective view of a composite spinal implant according to one embodiment of the invention.
Figure 18:
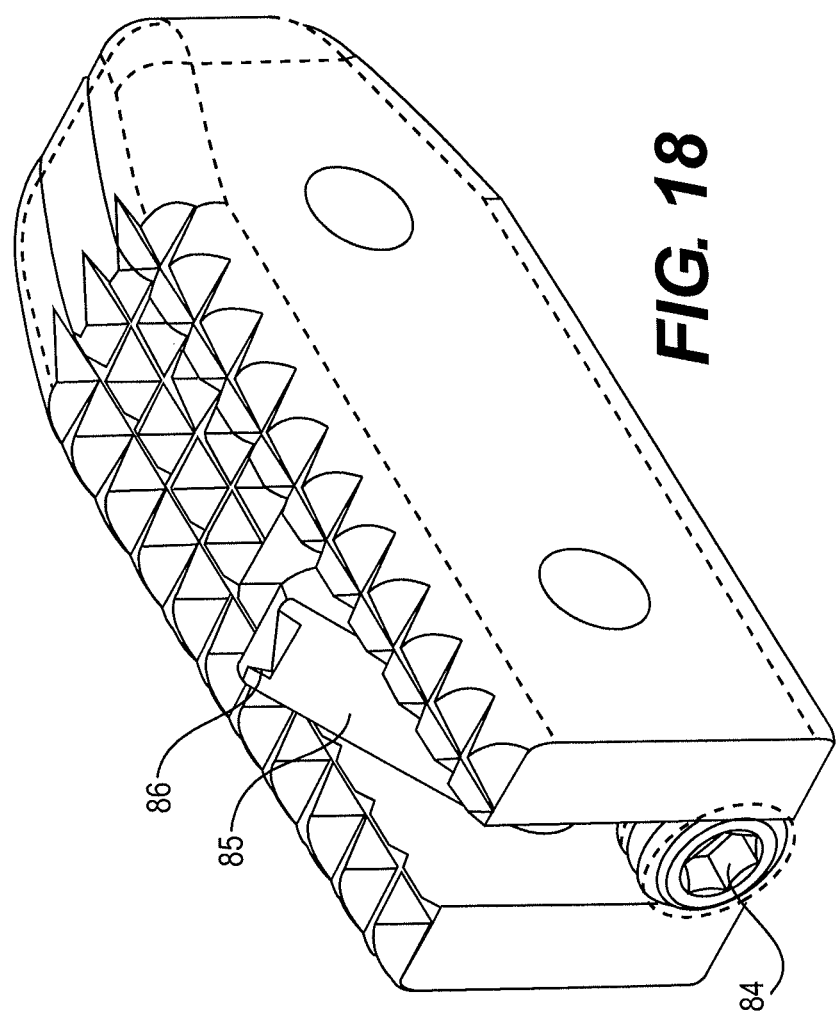
FIG. 18 presents a perspective view of a composite spinal implant according to one embodiment of the invention.
Figure 19:
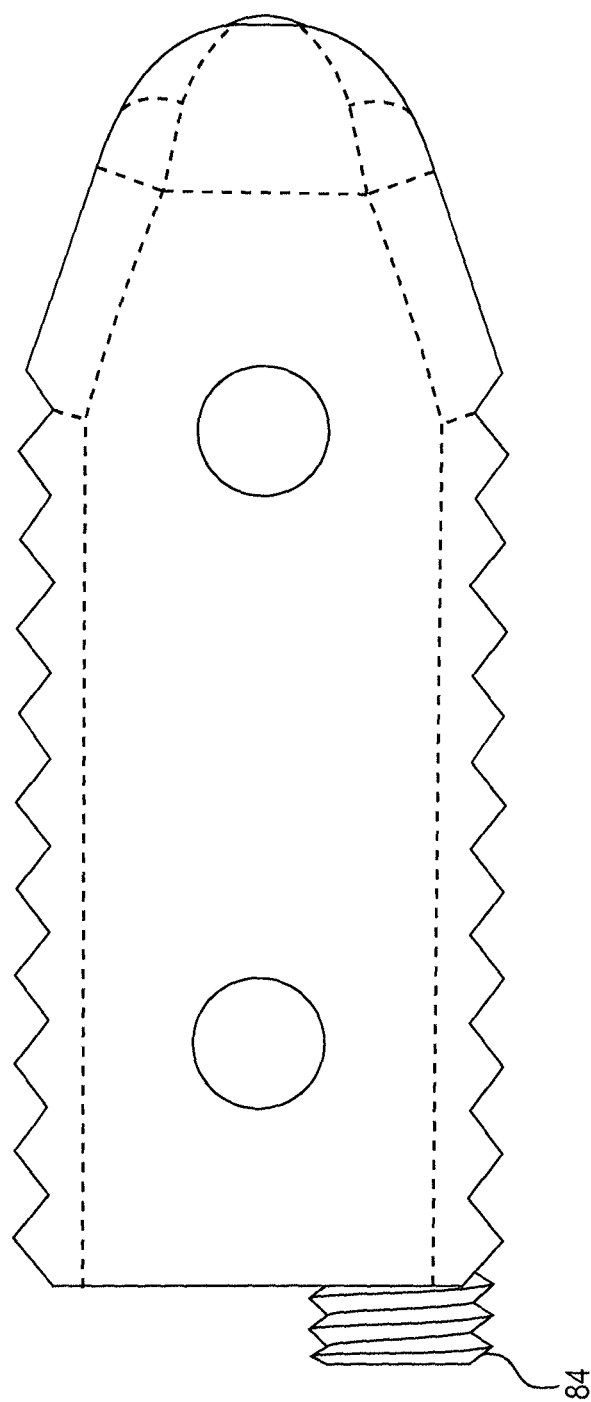
FIG. 19 presents a side view of a composite spinal implant according to one embodiment of the invention.
Figure 20:
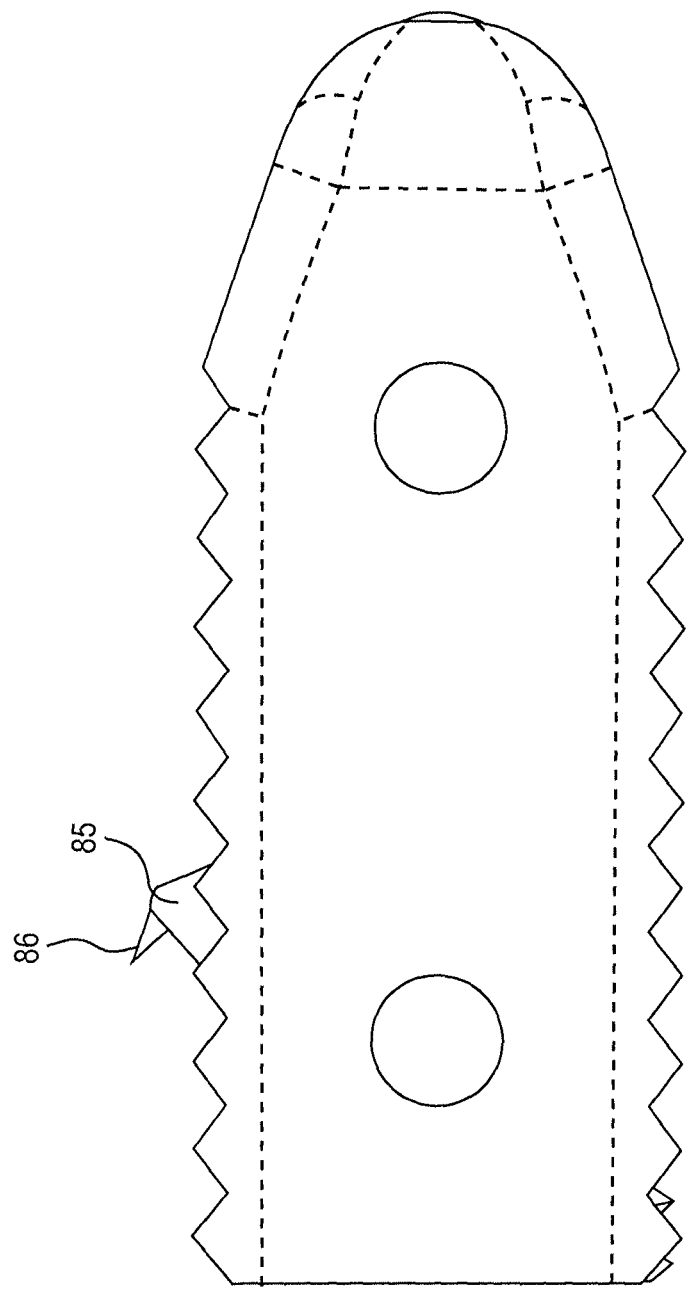
FIG. 20 presents a side view of a composite spinal implant according to one embodiment of the invention.
Figure 21:
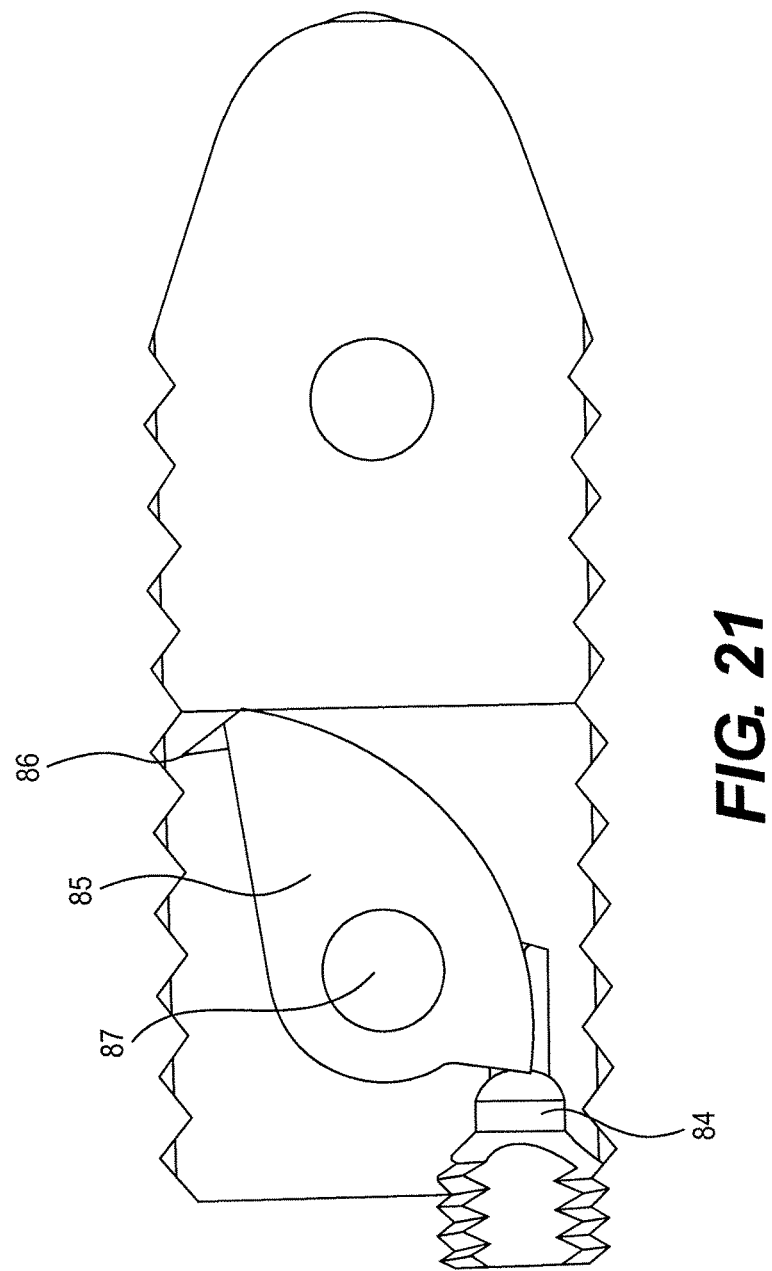
FIG. 21 presents a cut away side view of a composite spinal implant according to one embodiment of the invention.
Figure 22:
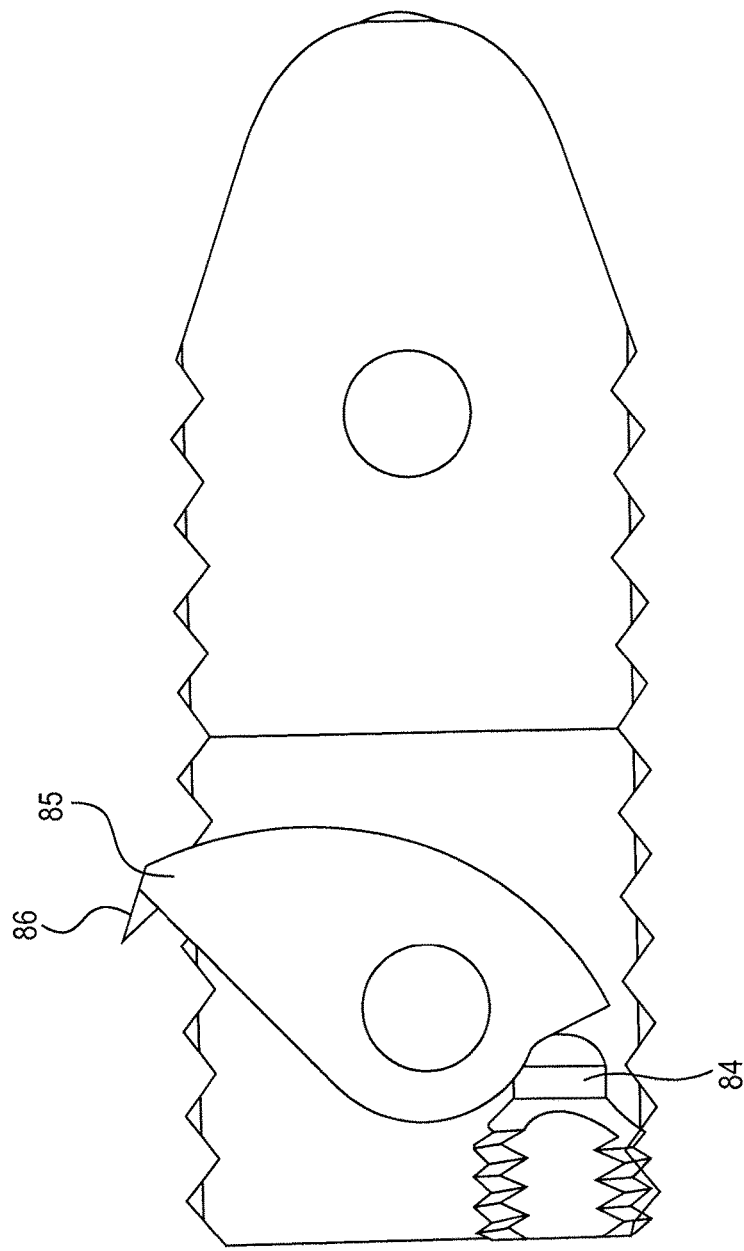
FIG. 22 presents a cut away side view of a composite spinal implant according to one embodiment of the invention.
Figure 23:
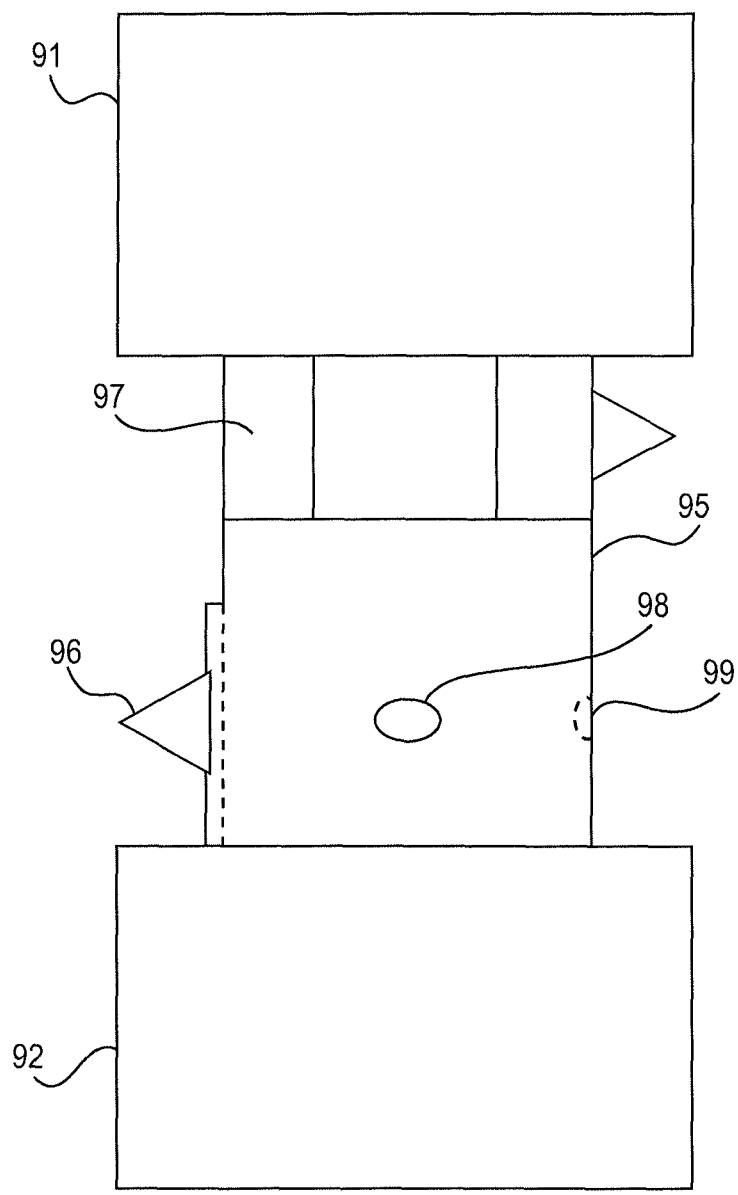
FIG. 23 presents a side view of composite medical implant according to one embodiment of the invention.
Figure 24:
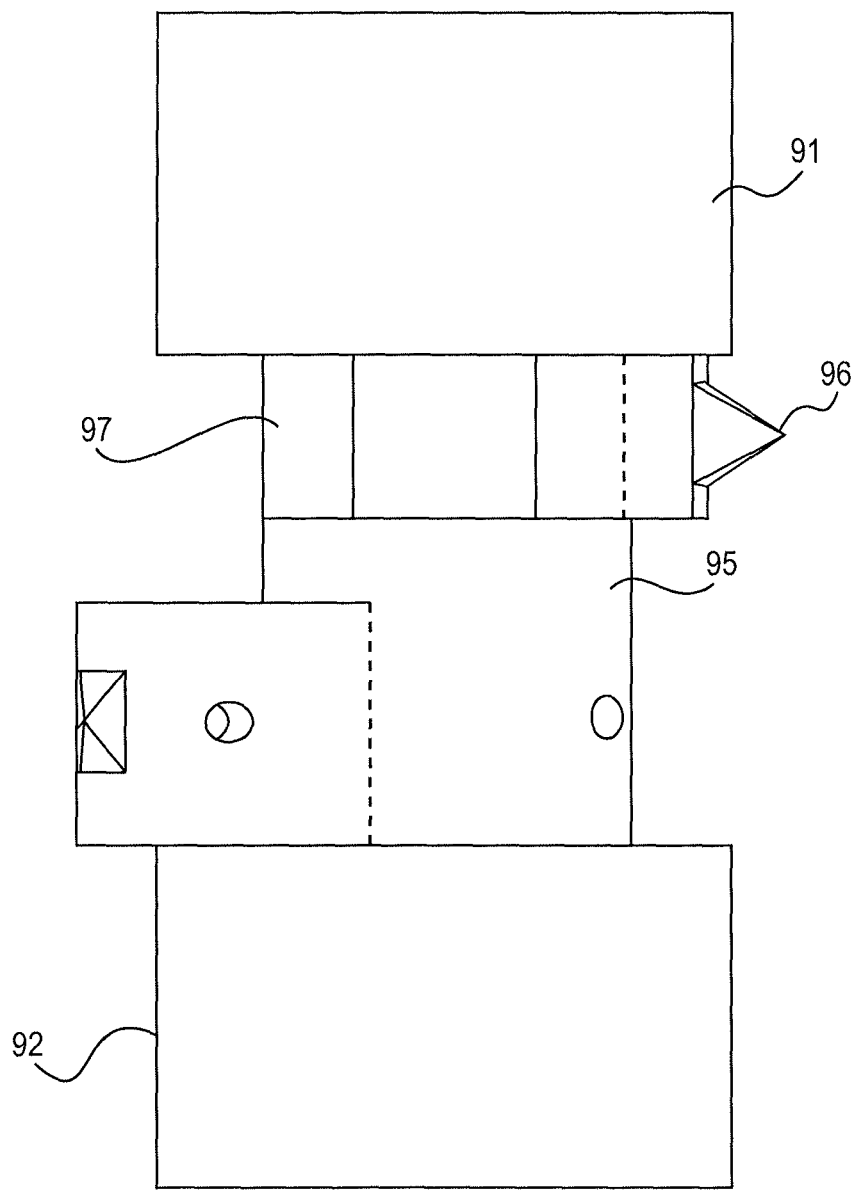
FIG. 24 presents a side view of composite medical implant according to one embodiment of the invention.
Figure 25:
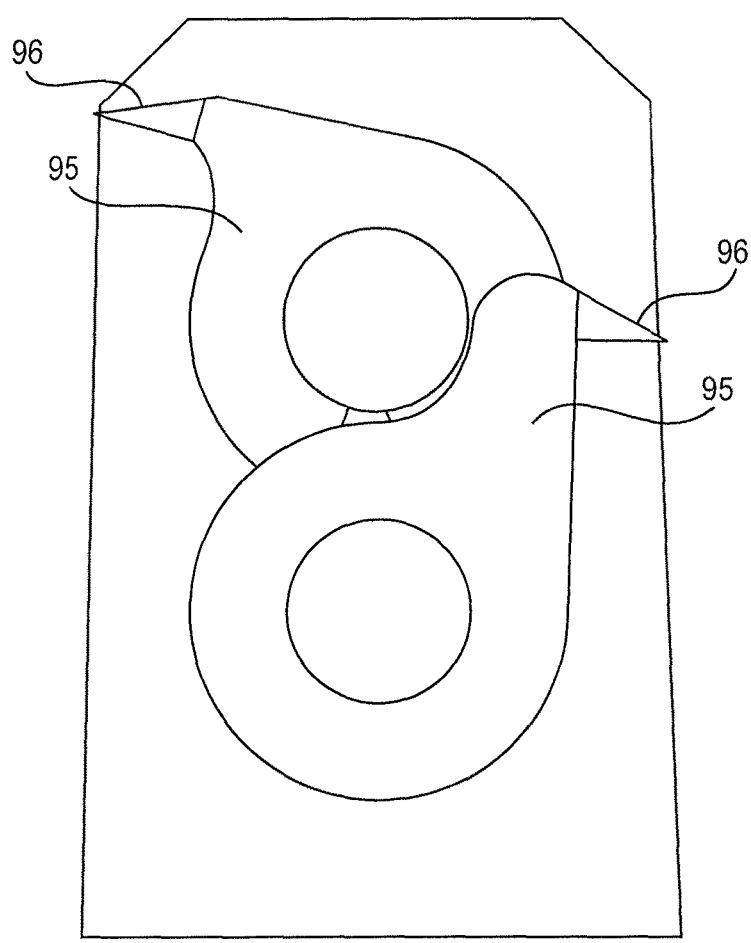
FIG. 25 presents a side cut away view of composite medical implant according to one embodiment of the invention.
Figure 26:
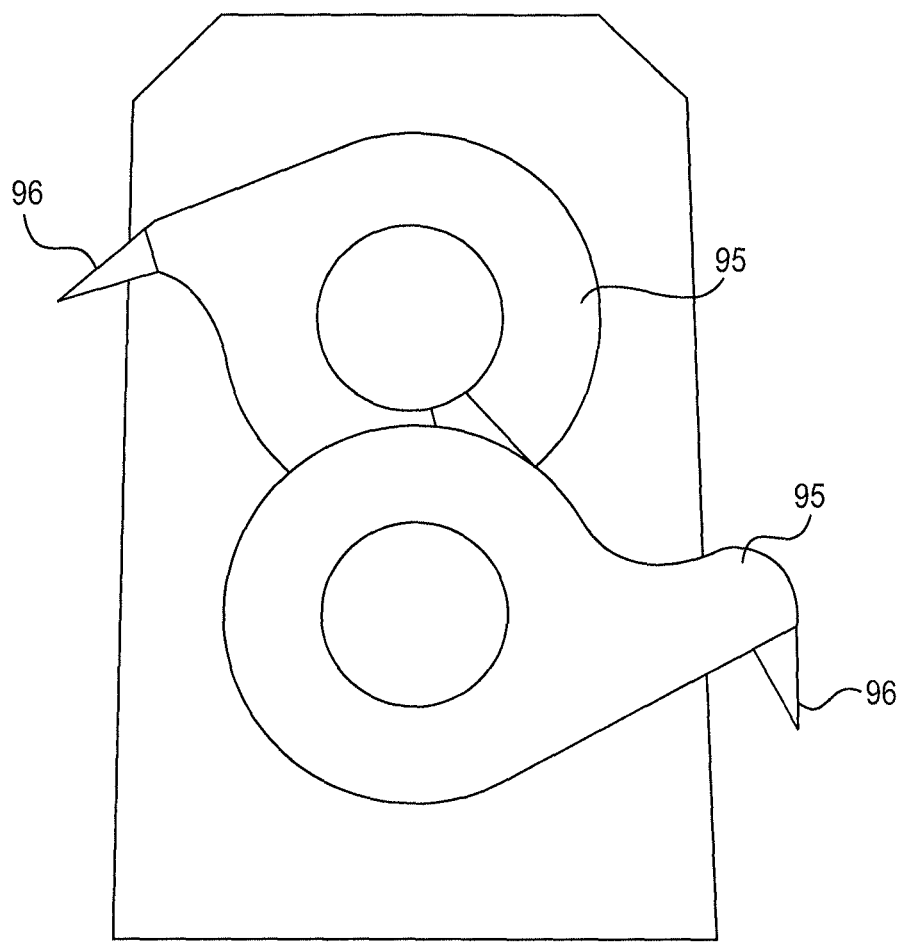
FIG. 26 presents a side cut away view of composite medical implant according to one embodiment of the invention.
Figure 27:
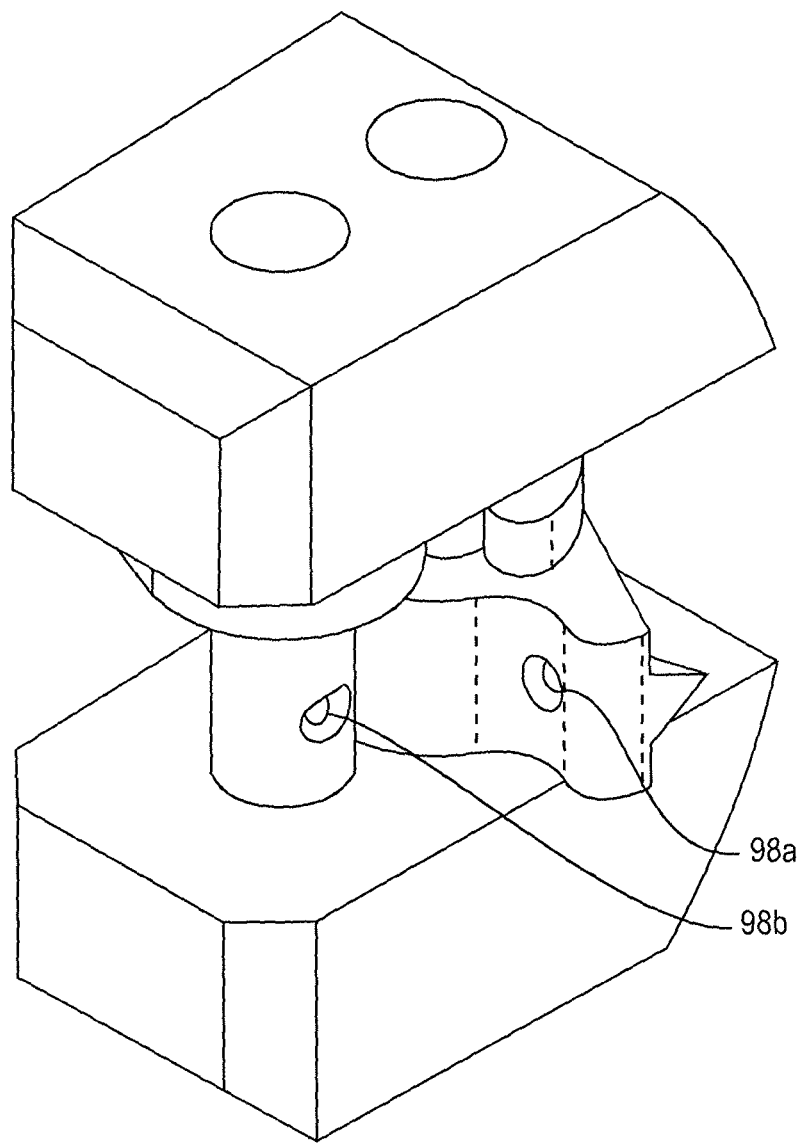
FIG. 27 presents a perspective view of composite medical implant according to one embodiment of the invention.
Figure 28:
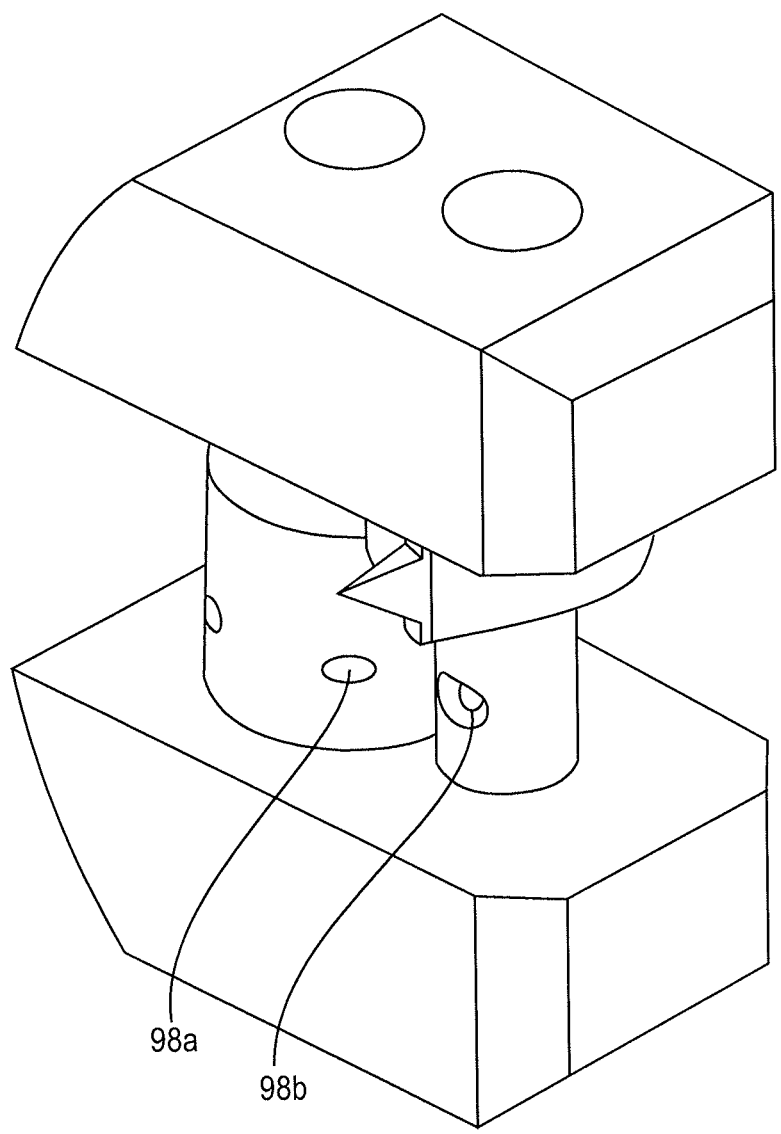
FIG. 28 presents a perspective view of composite medical implant according to one embodiment of the invention.
Figure 29:
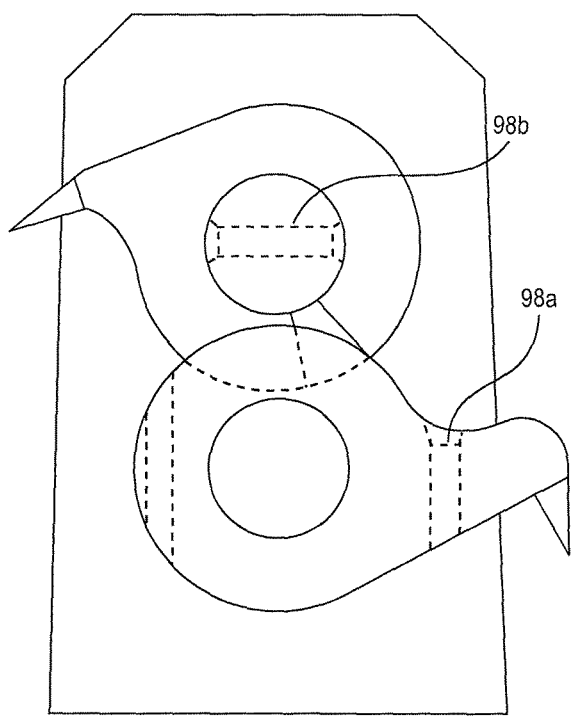
FIG. 29 presents a side cut away view of composite medical implant according to one embodiment of the invention.
Figure 31:
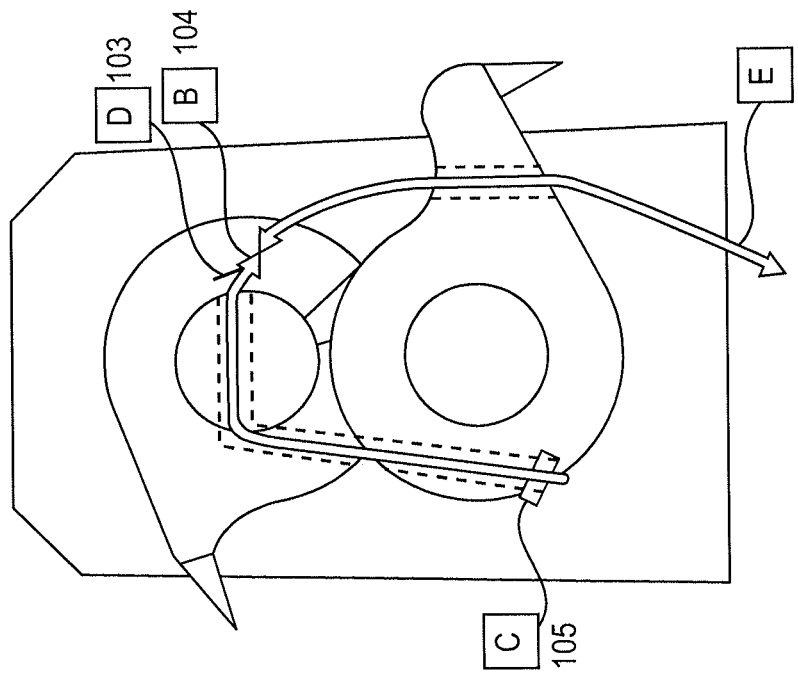
FIG. 31 presents a side cut away view of composite medical implant according to one embodiment of the invention.
Figure 30:
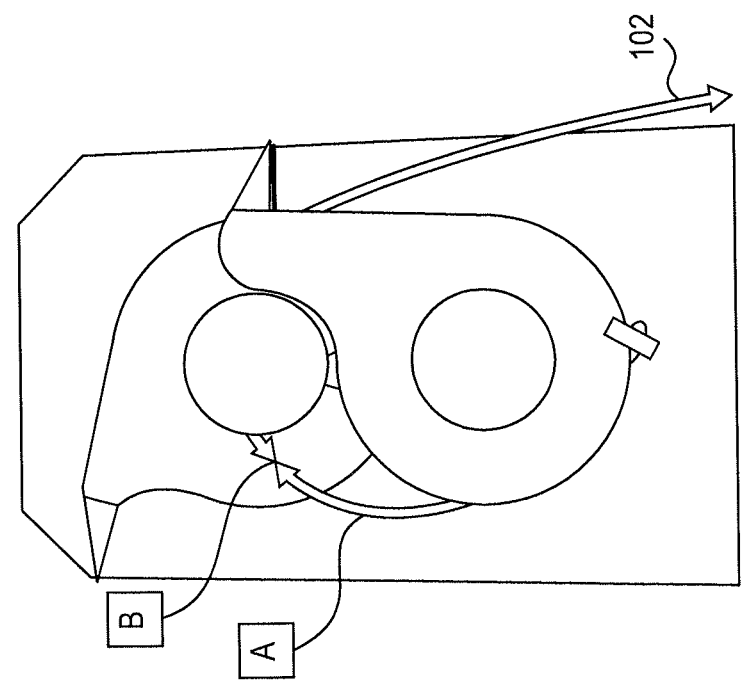
FIG. 30 presents a side cut away view of composite medical implant according to one embodiment of the invention.
Figure 33:
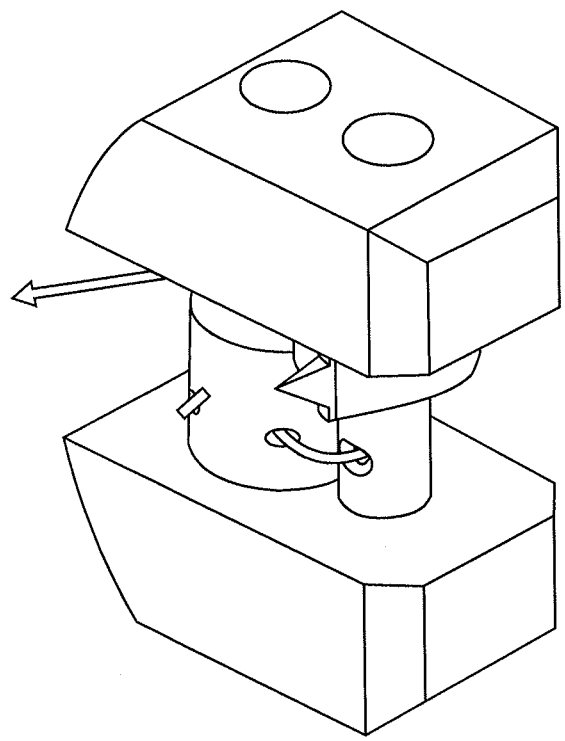
FIG. 33 presents a perspective view of composite medical implant according to one embodiment of the invention.
Figure 32:
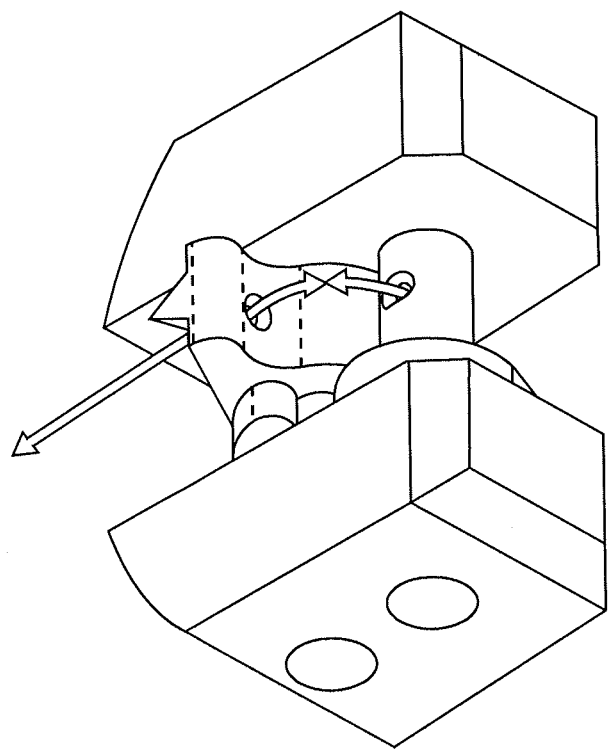
FIG. 32 presents a perspective view of composite medical implant according to one embodiment of the invention.
Figure 35:
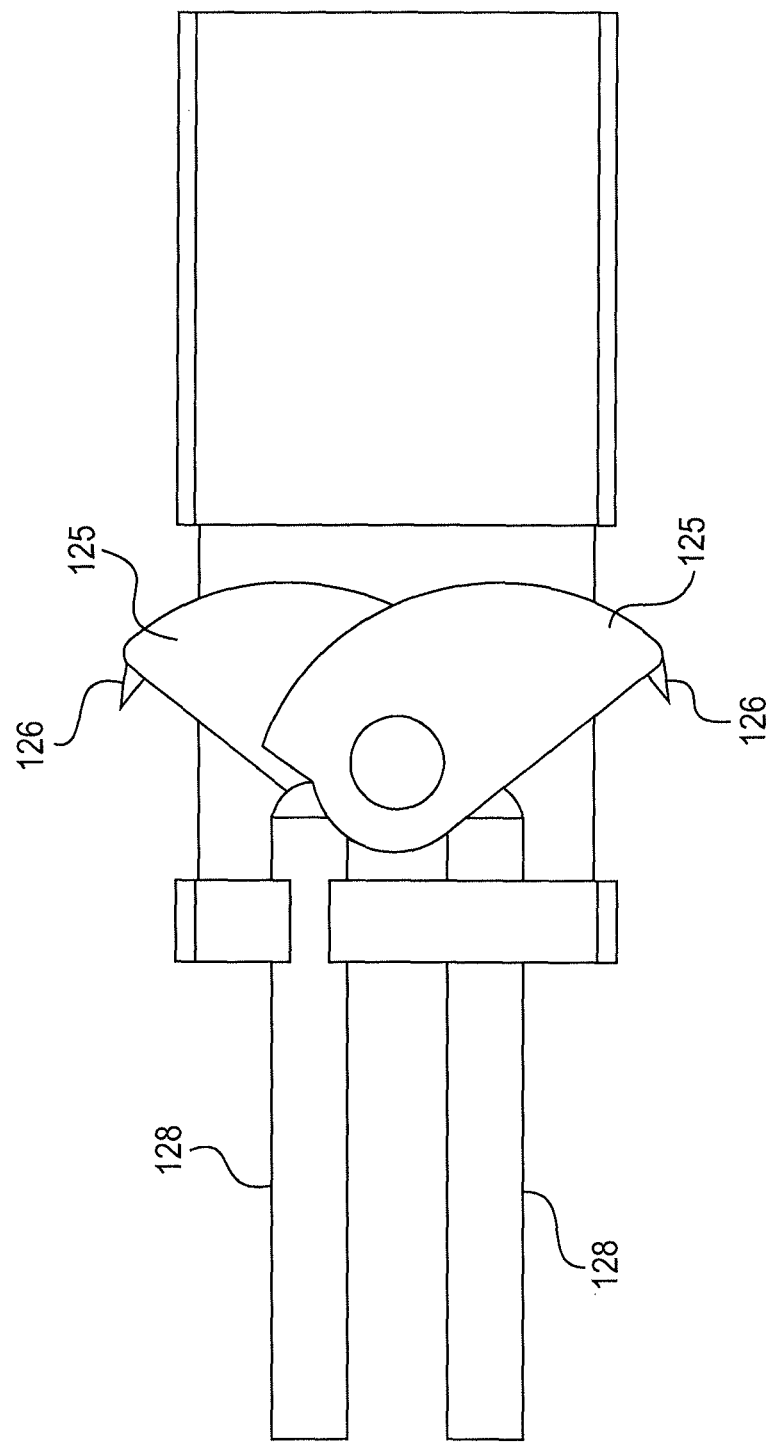
FIG. 35 presents a cut away side view of a composite medical implant according to one embodiment of the invention.
Figure 36:
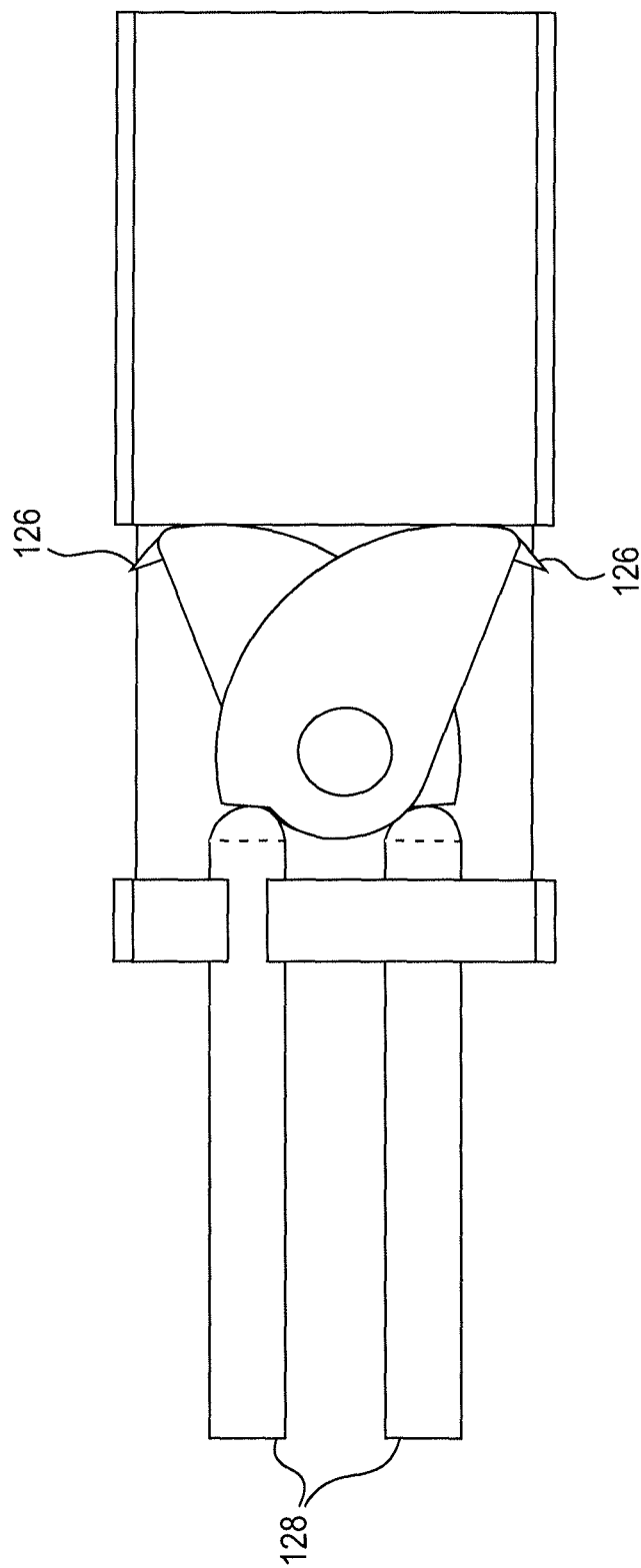
FIG. 36 presents a cut away side view of a composite medical implant according to one embodiment of the invention.
Figure 37:
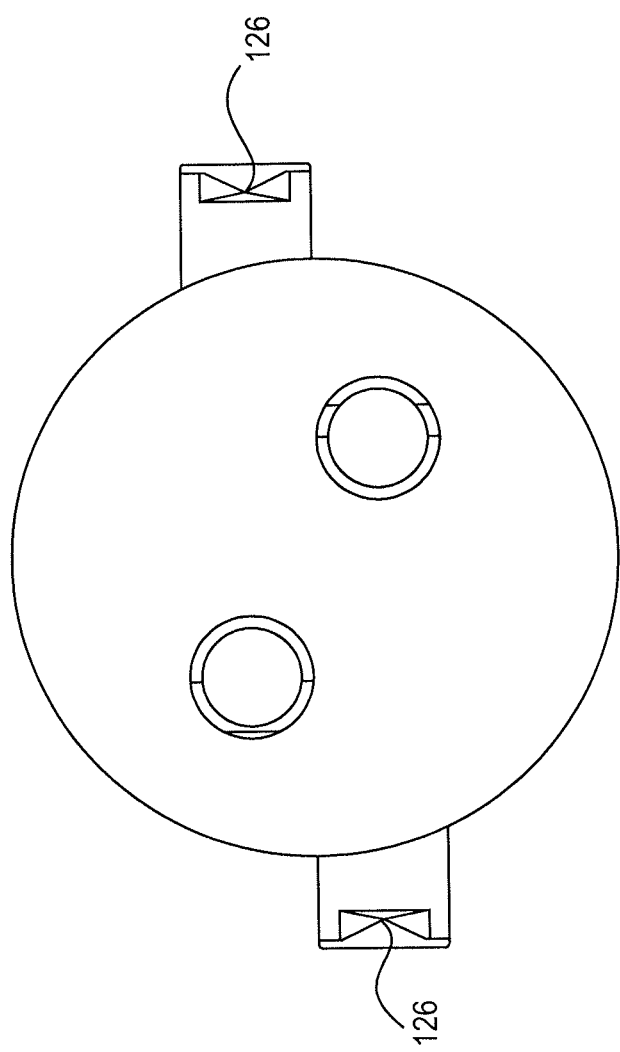
FIG. 37 presents a top view of a composite medical implant according to one embodiment of the invention.
Figure 38:
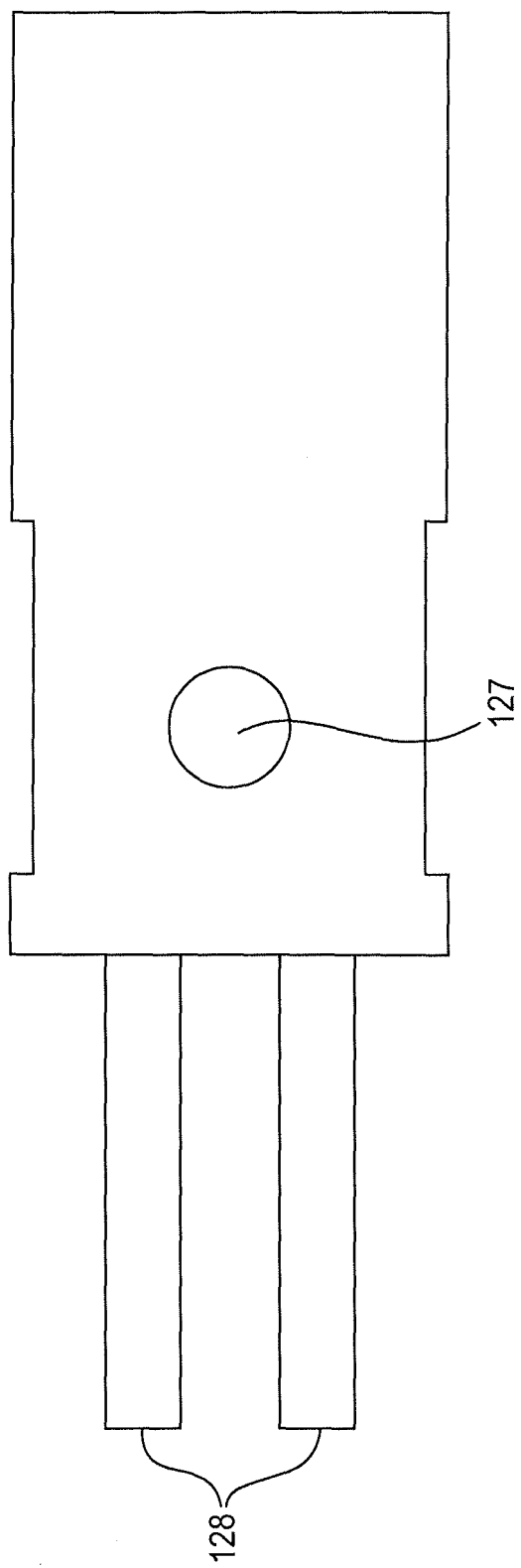
FIG. 38 presents a side view of a composite medical implant according to one embodiment of the invention.
Figure 39:
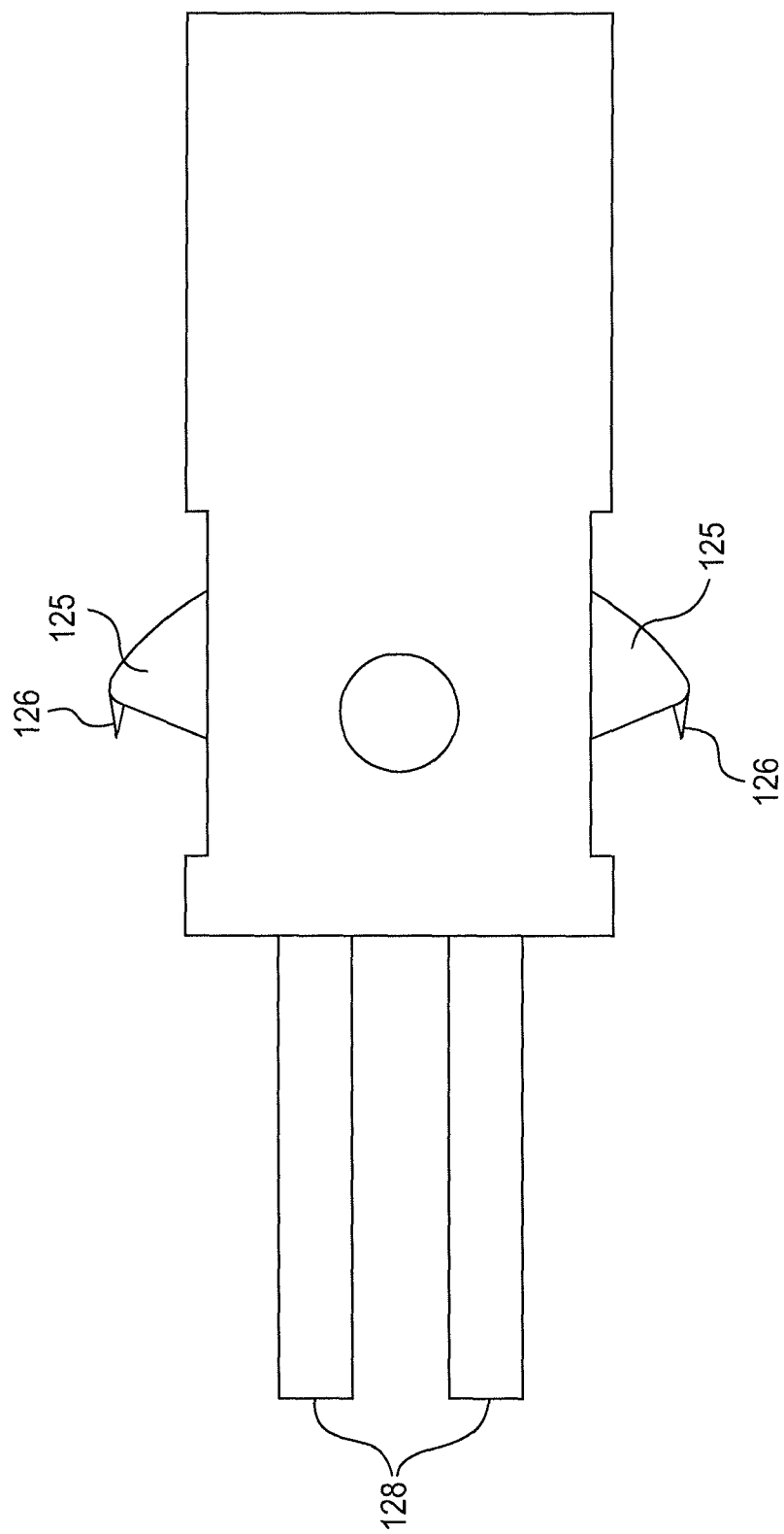
FIG. 39 presents a side view of a composite medical implant according to one embodiment of the invention.
Figures 40A, 40B:
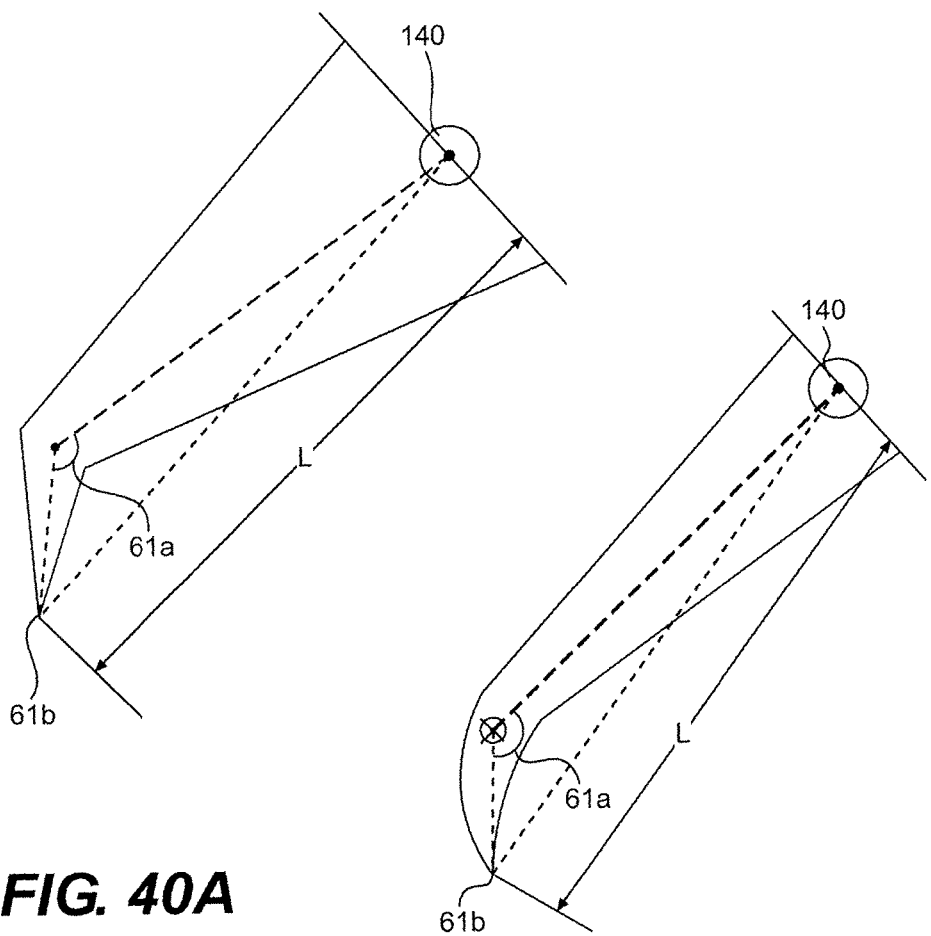
FIGS. 40A and 40B present an enlarged view of the double-angled sharp protrusion shown in FIG. 12.

FIGS. 12-16 show different views of a spinal implant (60) of the invention. The spinal implant of this embodiment may be used, for example, in anterior lumbar interbody fusion (ALIF) procedures. In the embodiments shown in these figures, the sharp protrusion (61), which is connected to the rotational fixation mechanism, may have a double angle. The first angle (61A) is sloped at an angle from about 5° to about 35° in the general direction of the protrusion. The second angle (61B) is sloped at an angle from about 10° to about 60° in the general direction of the protrusion. It has been discovered that angles within these ranges lead to optimal penetration and lodging into hard tissue. Hexagonal head screw (62) is used in this embodiment to engage with threads (65), pushing the rotational fixation mechanism (64) such that it rotates about an axis (e.g., pin) (63), urging the sharp protrusion (61) into a vertebral body or other hard tissue. As shown in FIG. 15, certain embodiments may employ two sharp protrusions, one on the superior portion of the implant and one on the inferior portion of the implant.

In embodiments of the invention, the sharp protrusion may curve inward toward the tip, rather than proceed toward the tip linearly as a result of one or more angles.

FIGS. 17-22 provide different views of a spinal implant of the invention. The spinal implant of this embodiment may be used, for example, in posterior lumbar interbody fusion (PLIF) procedures. Both the superior surface (81) and the inferior surface (82) are textured (83) and configured to contact a portion of hard tissue (e.g., a vertebral body). Screw (84) is used in this embodiment to engage with threads, pushing the rotational fixation mechanism (85) such that it rotates about axis (e.g., a pin or rod) (87), urging the sharp protrusion (86) into a vertebral body or other hard tissue.

FIGS. 23-33 provide different views of a spinal implant of the invention. The spinal implant of this embodiment may be used, for example, in anterior cervical fusion procedures. A first portion (91) and a second portion (92) are provided, each having an inferior and a superior surface. One or more axes (e.g., pins or rods) (97) may be used to hold together the first and second portion. One or more rotational fixation mechanisms (95) may be located between the first portion and the second portion, substantially centered on an axis. The rotational fixation mechanisms may comprise an opening through which the one or more axes traverse to secure the rotational fixation mechanisms in place. The rotational fixation mechanisms include at least one sharp protrusion (96) configured to penetrate a vertebral body. This is useful for providing stabilization of the spinal area where fusion occurs, and the resultant spinal bone graft may be used without additional stabilizing or anchoring structures, such as supporting plates or screws.

In certain embodiments (see e.g., FIGS. 30-33), a wire (102) is used to engage with the rotational fixation mechanisms, pulling the rotational fixation mechanism (95) to rotate about their axis (e.g., pin), urging the sharp protrusion (96) into a vertebral body or other hard tissue. The wire (102) may be made of a variety of materials, including, for example, a composite material such as FiberWire, Kevlar or a carbon fiber weave. The wire (102) may be secured in the end (105) of a rotational fixation mechanism and may be threaded through holes in the rotational fixation mechanisms (98A) and axis (98B). The wire contains a directional barb (103) that prevents the rotational fixation mechanisms from reversing direction once the barb (103) is pulled through the opening in the axis. The wire also may have a break point (104) at a designated spot, the break point designed to separate at a predetermined tension in the wire, thus locking the sharp protrusions into position. Upon implantation, a surgeon may pull the wire at the appropriate tension such that the sharp protrusions will penetrate and be lodged into the vertebral bodies. A portion of the wire may be designed to sever at the break point.

FIGS. 34-39 provide views of a compound medical implant that may be used for fixation and integration with hard tissue at different locations in the body, including, but not limited to, the knee, ankle, hip, shoulder, elbow, fingers and vertebrae. The implant comprises an implant body (121) and rotational fixation mechanisms (125), which rotate around an axis (127) and are attached to sharp protrusions (126). External pins (128) may be used to push the respective rotational fixation mechanisms (125), thus allowing the fixation mechanisms to rotate about their respective axes, urging the sharp protrusions into hard tissue.

The implants of the invention can be used, for example, at a knee joint during an operation such as cruciate ligament reconstruction. In such an operation, the implants of the invention may act as bone plugs, inserted into bone tunnels drilled into the relevant bones surrounding the knee (e.g., the tibia or femur). One common approach to cruciate ligament reconstruction is the use of the patellar tendon to form a bone-tendon-bone graft. This involves cutting out a bone block from the top of the patella. The medical implants of the invention may be used in a bone-tendon-bone composite graft for use in cruciate ligament reconstruction along with a tibial drill guide for forming the tibial tunnel, a trefoil rasp for forming channels in the bone tunnels and a bone block drill guide for forming the bone plugs of the graft. In some aspects, a bone tunnel may be formed in each of two bones of the joint. In knee surgery, these are the femur and the tibia. Preferably, the bone tunnel is formed by drilling a core out through the bone such that the core might be used to form the bone plug in the composite graft. The bone plugs are machined to form two longitudinal substantially parallel grooves opposite one another. At least one ligament replacement, such as a semitendinosus tendon, and/or gracilis, may be extended between both of two bone plugs along the parallel grooves in each plug. The ligament replacement may be attached to the two bone plugs. Each bone plug may be inserted into one of the bone tunnels and secured therein by an interference screw. The use of the bone-tendon-bone composite graft of the invention results in a reconstructed cruciate ligament. The aforementioned embodiments may include two or more rotational fixation mechanisms (e.g., six, eight or 10), each including a sharp protrusion. The two or more rotational fixation mechanisms may share an axis, or they may be centered on separate axes such that they are in series.

In some applications, it may be difficult for the implants of the invention to penetrate hard tissue (e.g., cartilage and cortical bone). Thus, to facilitate penetration of a sharp protrusion into hard tissue (e.g., in a vertebral body or a long bone) one may use a drill guide with or without a template implant containing a drill hole guide channel. In one aspect, a surgeon may position a drill guide template graft in the appropriate location (e.g., the vertebrae between L4 and L5). For example, the drill guide template then may be used to drill a preliminary hole into L4. The drill guide template is then withdrawn prior to insertion of the implant, whereby the sharp protrusion may be maneuvered to penetrate the hard tissue through the pre-drilled preliminary holes.

In embodiments of the invention, the sharp protrusions may include teeth or barbs to prevent reverse migration once the protrusions are lodged into hard tissue.

It is to be understood that the scope of the present invention is not to be limited to the specific embodiments described above. The invention may be practiced other than as particularly described and still be within the scope of the accompanying claims.

What is claimed is:

1. A medical implant for fixation and integration with hard tissue, the medical implant comprising:

a first portion having an inferior and superior surface;
a second portion having an inferior and superior surface;
one or more pins for holding together the first portion and the second portion, at least one of said one or more pins comprising an opening transverse to the axial direction of the pin; and
one or more rotational fixation mechanisms located between the first portion and the second portion, said one or more rotational fixation mechanisms comprising a first opening through which the one or more pins traverse and one or more second openings through which a wire may traverse,
wherein the one or more rotational fixation mechanisms comprise at least one sharp protrusion, each sharp protrusion configured to penetrate and become lodged into hard tissue,
wherein one end of the wire is secured to one rotational fixation mechanism and the other end of the wire is pulled through the openings in the rotational fixation mechanisms and the pin,
wherein the wire comprises a directional barb used to prevent the rotational fixation mechanisms from reversing direction once the barb is pulled through the opening in the one or more pins, and
wherein the wire has a break point designed to separate at a predetermined wire tension, thus locking the sharp protrusions into position.

2. The medical implant of claim 1 wherein the first and second portion, the one or more pins and the one or more rotational fixation mechanisms are independently made of a member selected from the group consisting of cortical bone, a biocompatible metal and a biocompatible polymer.

3. The medical implant of claim 2 wherein the first and second portion, the one or more pins and the one or more rotational fixation mechanisms are made of cortical bone.

4. The medical implant of claim 2 wherein the rotational fixation mechanism is made of a biocompatible metal.

5. The medical implant of claim 1 wherein the at least one sharp protrusion has a length ranging from about 0.5 mm to about 0.8 cm.

6. The medical implant of claim 1, wherein the hard tissue is a vertebral body, and wherein the at least one sharp protrusion penetrates at least one of two vertebral bodies, one on the superior side of the implant and one on the inferior side of the implant.

* * * * *